US010772903B2

(12) United States Patent
Shiao et al.

(10) Patent No.: US 10,772,903 B2
(45) Date of Patent: Sep. 15, 2020

(54) TARGETING FUNGI IN COMBINATION WITH CANCER THERAPY

(71) Applicant: Cedars-Sinai Medical Center, Los Angeles, CA (US)

(72) Inventors: Stephen Shiao, Los Angeles, CA (US); David Underhill, Tarzana, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 31 days.

(21) Appl. No.: 15/702,141

(22) Filed: Sep. 12, 2017

(65) Prior Publication Data

US 2018/0071329 A1    Mar. 15, 2018

Related U.S. Application Data

(60) Provisional application No. 62/393,546, filed on Sep. 12, 2016.

(51) Int. Cl.

| | |
|---|---|
| *A61K 31/7048* | (2006.01) |
| *A61K 31/513* | (2006.01) |
| *A61K 31/4196* | (2006.01) |
| *A61P 35/00* | (2006.01) |
| *A61P 31/10* | (2006.01) |
| *A61K 45/06* | (2006.01) |
| *A61N 5/10* | (2006.01) |
| *A61K 36/06* | (2006.01) |

(52) U.S. Cl.
CPC ...... *A61K 31/7048* (2013.01); *A61K 31/4196* (2013.01); *A61K 31/513* (2013.01); *A61K 36/06* (2013.01); *A61K 45/06* (2013.01); *A61N 5/10* (2013.01); *A61P 31/10* (2018.01); *A61P 35/00* (2018.01)

(58) Field of Classification Search
None
See application file for complete search history.

(56) References Cited

U.S. PATENT DOCUMENTS 8,871,226 B2 * 10/2014 Mahboubi ............ A61K 31/00
424/274.1
2005/0049207 A1   3/2005 Kaufmann

OTHER PUBLICATIONS

Diosma et al., "Yeasts from kefir grains: isolation, identification, and probiotic characterization" World Journal Microbiol Biotechnol vol. 30 pp. 43-53 (Year: 2014).*
Cuttino et al., "Multi-Institutional Experience Using the Mammosite Radiation Therapy System in the Treatment of Early-Stage Breast Cancer: 2-Year Results" Int J Radiation Oncology Biol Phys7-114 (Year: 2008).*
Keisch et al., "Thirty-Nine Month Results with the MammoSite Brachytherapy Applicator: Details Regarding Cosmesis, Toxicity and Local Control in Partial Breast Irradiation" Int J Radiation Oncology Biol Phys vol. 63 No. 2S, p. s6 (Year: 2005).*
Huang et al., "Antibiotic prophylaxis in prosthesis-based mammoplasty: A systematic review" International Journal of Surgery vol. 15 pp. 31-37 (Year: 2015).*
Moreno et al., "Study of Immune Cells Involved in the Antitumor Effect of Kefir in a Murine Breast Cancer Model" Journal of Dairy Science vol. 90 pp. 1920-1928 (Year: 2007).*
Patiroglu et al., "Multiple Fungal Brain Abscesses in a Child with Acute Lymphoblastic Leukemia" Mycopathologia vol. 174 pp. 505-509 (Year: 2012).*
Takahashi et al., "Radiosensitization of gliomas by intracellular generation of 5-fluorouracil potentiates prodrug activator gene therapy with a retroviral replicating vector" Cancer Gene Therapy vol. 21 pp. 405-410 (Year: 2014).*
Marklund et al., "Cisplatin-Induced Apoptosis of Mesothelioma Cells is Affected by Potassium Ion Flux Modulator Amphotericin B" International Journal of Cancer vol. 93 pp. 577-583 (Year: 2001).*
Yamaguchi et al., "Immunomodulating Activity of Antifungal Drugs" Annals of the New York Academy of Sciences, vol. 685, pp. 447-457 (Year: 1993).*
De Pauw, B.E. "Treatment of Documented and Suspected Neutropenia-Associated Invasive Fungal Infections" Journal of Chemotehrapy vol. 13 No. 1 pp. 181-192 (Year: 2001).*
Mucke et al., "Fluconazole prophylaxis in patients with head and neck tumours undergoing radiation and radiochemotherapy" Mycoses vol. 41 pp. 421-423 (Year: 1998).*
Pantziarka et al., Repurposing Drugs in Oncology (ReDO)—Itraconazole as an Anti-Cancer Agent, eCancer, 2015, vol. 9, p. 521.
Sivan et al., Commensal Bifidobacterium Promotes Antitumor Immunity and Facilitates Anti-PD-L1 Efficacy, Science, 2015, vol. 350(6264), pp. 1084-1089.

* cited by examiner

*Primary Examiner* — Eric Olson
(74) *Attorney, Agent, or Firm* — Linda B. Huber; Nixon Peabody LLP

(57) ABSTRACT

Described herein are methods for the treatment of cancer by modulating fungal populations to enhance the therapeutic response to a cancer therapy. In particular, the present invention discloses modulating the fungal microbiome in combination with a cancer therapy to enhance the anti-tumor effect.

21 Claims, 34 Drawing Sheets

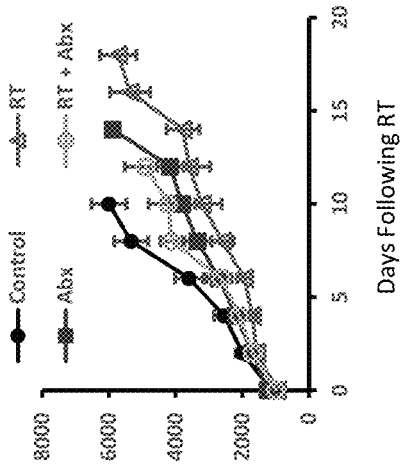
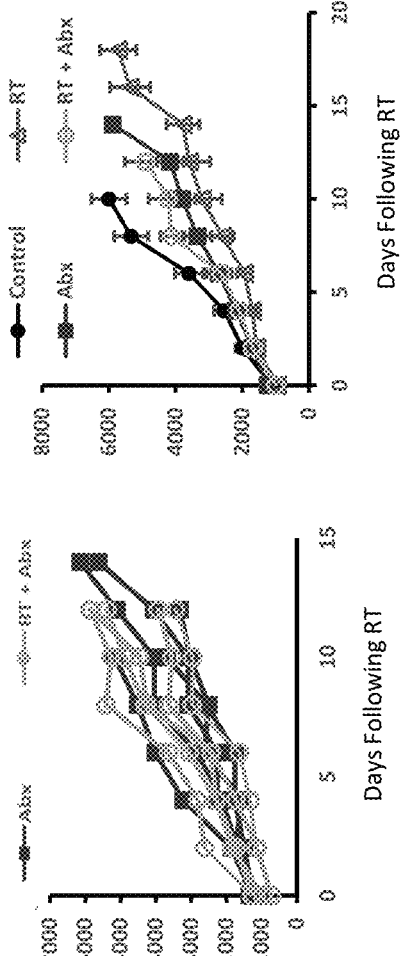
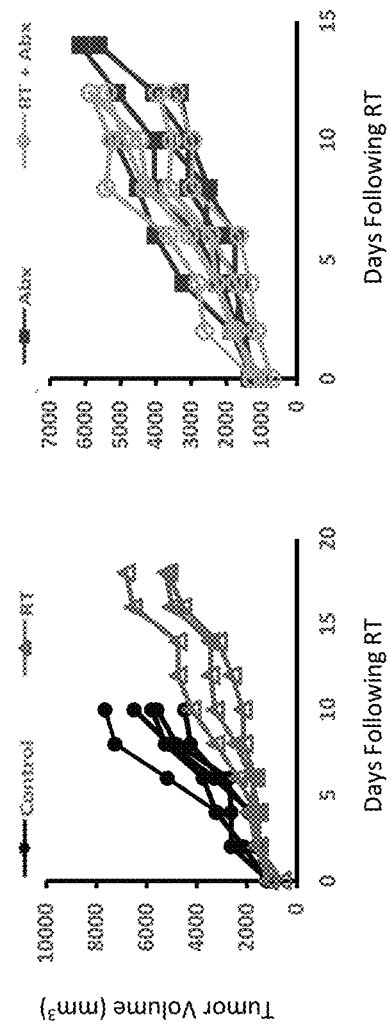
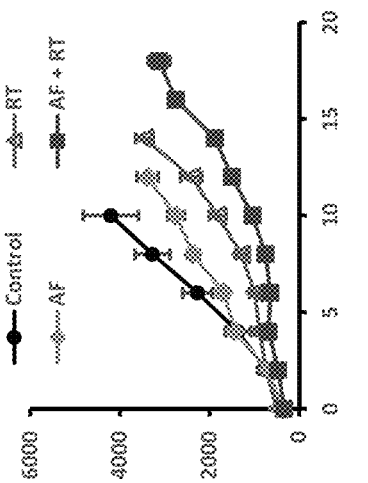
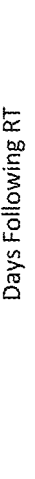
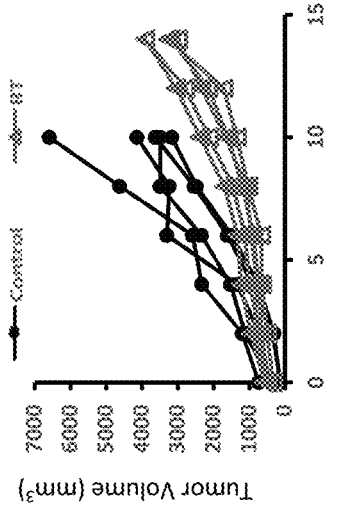

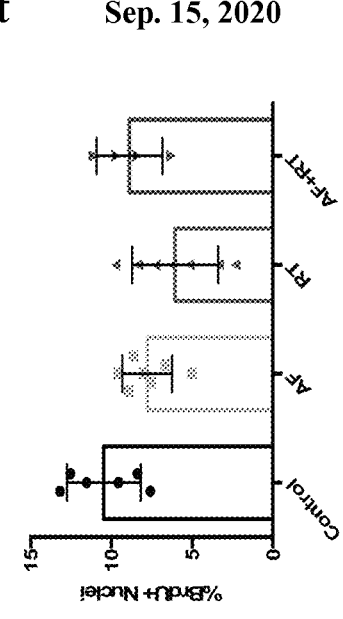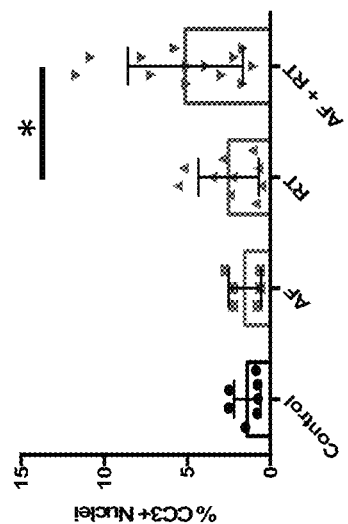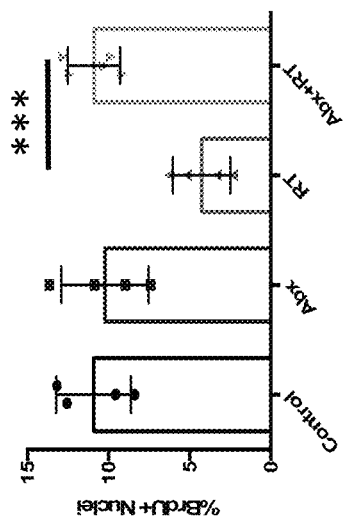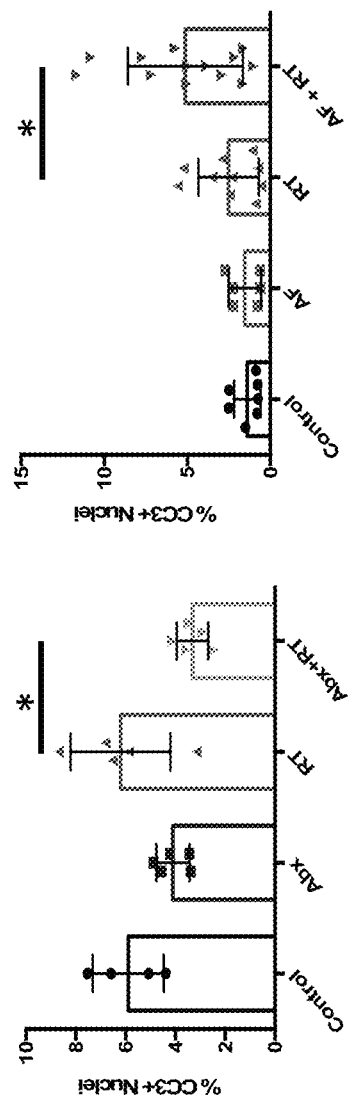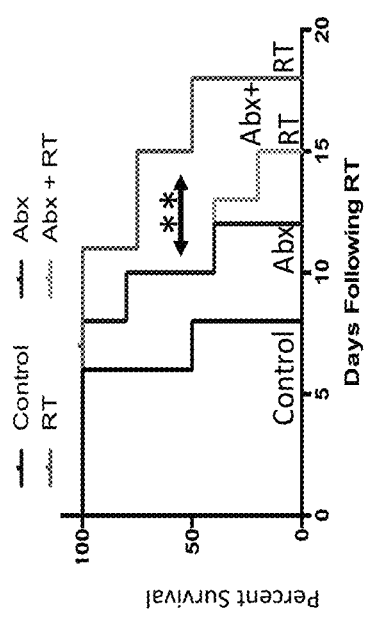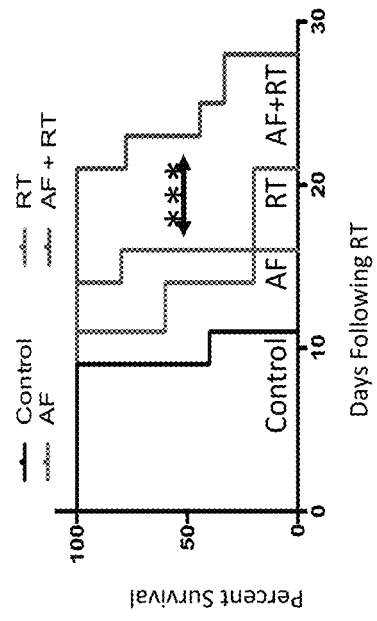
Fig. 26G  Fig. 26I  
Fig. 26H  Fig. 26J

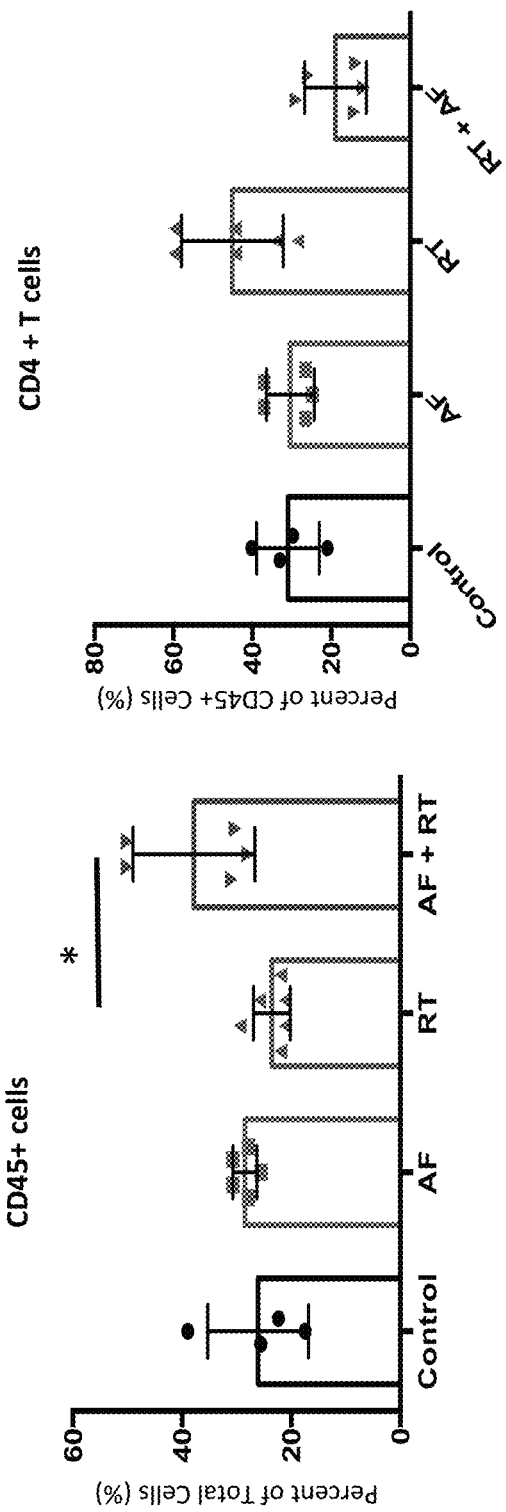
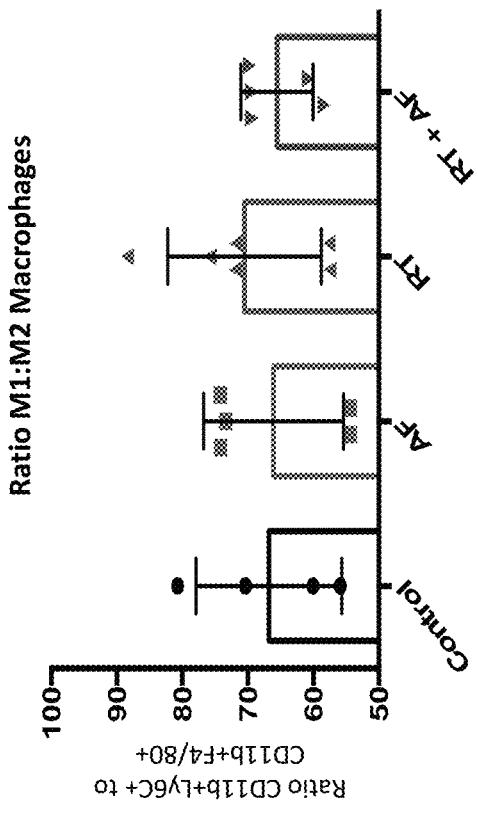
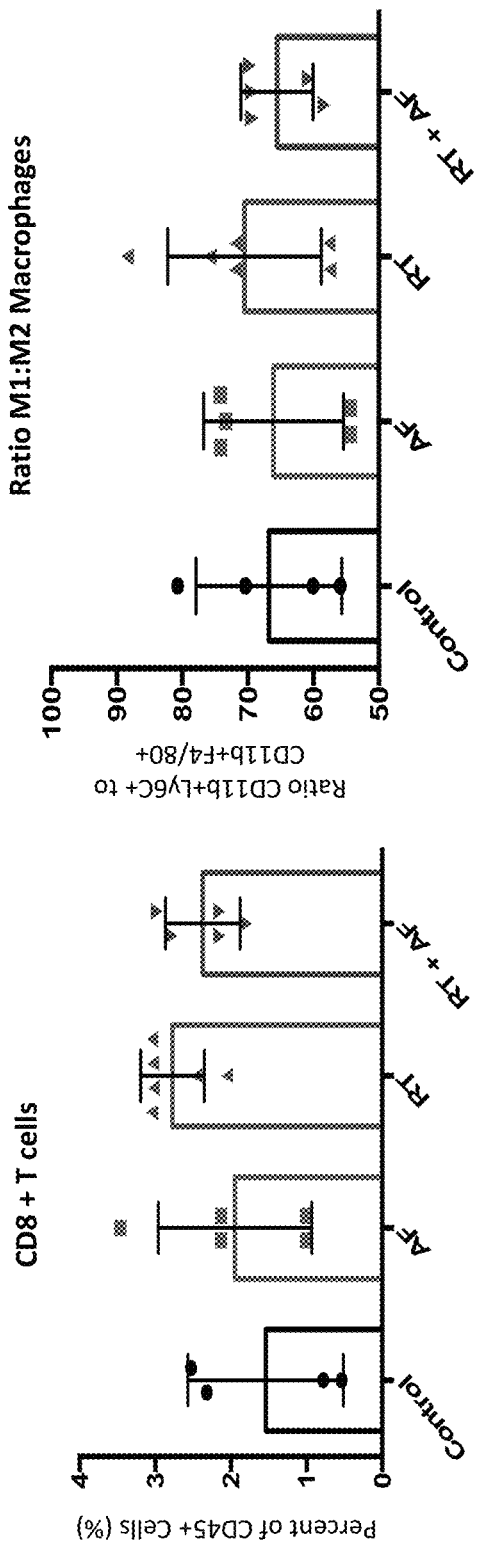
Fig. 28E, Fig. 28F, Fig. 28G, Fig. 28H

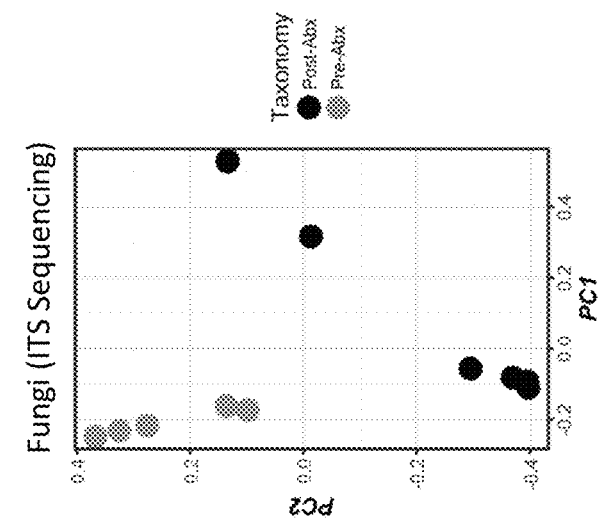
Fig. 29A
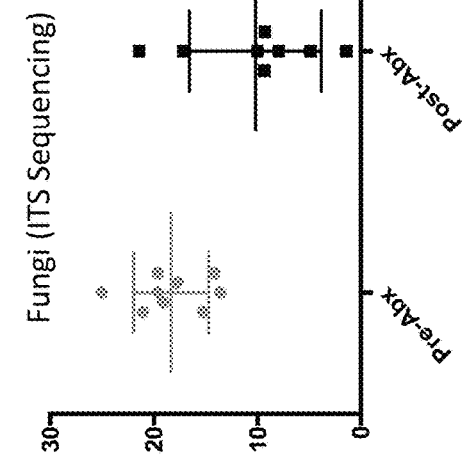
Fig. 29B
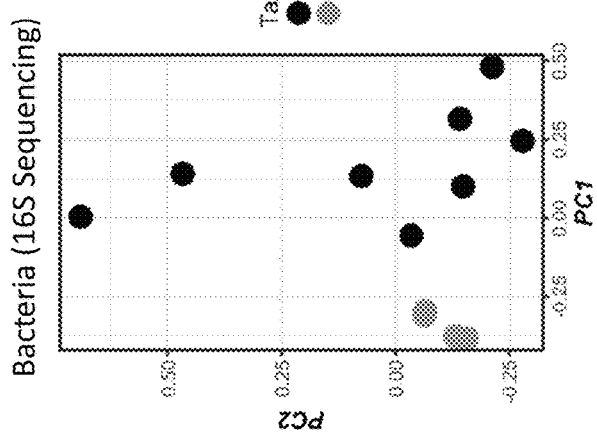
Fig. 29C
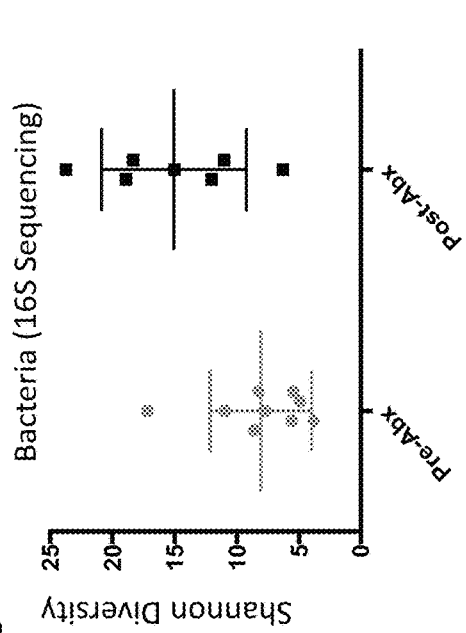

TARGETING FUNGI IN COMBINATION WITH CANCER THERAPY

CROSS-REFERENCE TO RELATED APPLICATION

This application claims the benefit under 35 U.S.C. § 119(e) of U.S. Provisional Patent Application No. 62/393,546 filed on Sep. 12, 2016, which is incorporated herein by reference in its entirety.

STATEMENT REGARDING FEDERALLY SPONSORED RESEARCH OR DEVELOPMENT

This invention was made with government support under Grant No. CA191139 awarded by the National Institutes of Health. The government has certain rights in the invention.

FIELD OF INVENTION

This invention relates to the use of combined treatments for the enhancement of cancer therapy.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Breast cancer is the most common cancer and second leading cause of cancer death of women in North America with an estimated 226,000 new diagnoses per year in 2013. Over 50% of woman diagnosed with breast cancer receive radiation therapy (RT) and chemotherapy such as doxorubicin, cyclophosphamide and paclitaxel following surgery with demonstrated survival advantage in numerous randomized trials. However despite recent advances in treatment, the fact that 40% of women with locally advanced cancer still succumb to disease highlights the need for new therapeutic approaches and identification of new therapeutic targets. One such target is the immune microenvironment of breast tumors. It has been suspected that inflammation drives the development of cancer; however, it has only been recently recognized that the immune system also regulates the response to standard treatments including RT and chemotherapy. Despite this recognition, research in radiation and chemotherapy still remains largely focused on the effects of these agents on tumor cells themselves and little is known about which cells and pathways of the immune system determine the response of tumors to cytotoxic therapy. There exists a need for treatment strategies to enhance the therapeutic response of cancer therapy.

SUMMARY OF THE INVENTION

Various embodiments of the present invention provide for a method of treating cancer or reducing tumor size in a subject in need thereof, comprising administering a therapeutically effective amount of a composition that modulates a fungal population and administering a therapeutically effective amount of a cancer therapy. In various embodiments, the cancer is breast cancer.

In various embodiments, the administration of the composition modulates a fungal population and enhances the therapeutic response to the cancer therapy. In various other embodiments, the administration of the composition modulates a fungal population and enhances the anti-tumor response to the cancer therapy.

In various embodiments, the composition that modulates the fungal population is an anti-fungal agent and/or a fungal probiotic. In various other embodiments, the anti-fungal agent causes a decrease in the fungal population. In other embodiments, the fungal populations decreased are *Aspergillus, Cladosporium, Phoma, Guehomyces, Candida tropicalis* or combinations thereof. In yet other embodiments, the anti-fungal agent is fluconazole, 5-flurocytosine, amphotericin B or a combination thereof.

In various embodiments, the fungal probiotic causes an increase in the fungal population. In various other embodiments, the fungal populations increased are *Wallemia, Epicoccum, Apergillus, Apergillus amstelodami, Saccharomyces cerevisiae* or combinations thereof.

In various embodiments, the cancer therapy is radiation therapy, chemotherapy, immunotherapy and/or targeted therapy. In various embodiments, the cancer therapy is radiation therapy (RT). In various embodiments, RT is administered in a dosage between 2 Gy to 34 Gy. In yet other embodiments, the RT is administered for 1 to 7 weeks.

In various embodiments, the method further comprises administering a therapeutically effective amount of an antibiotic, and the antibiotic is not a combination of vancomycin, streptomycin, ampicillin, and metronidazole, is not vancomycin, colistin, and ampicillin, is not vancomycin, imipenem/cilastin, and streptomycin, is not vancomycin, imipenem/cilastin, and ampicillin, is not ampicillin, streptomycin, and colistin, or is not vancomycin, imipenem/cilastatin, and neomycin, if the cancer therapy is RT.

Various embodiments of the present invention also provide for a method of enhancing the efficacy of a cancer therapy in a subject in need thereof, comprising administering a therapeutically effective amount of an anti-fungal agent and administering a therapeutically effective amount of a cancer therapy. In various embodiments, the subject is a subject with breast cancer.

In various embodiments, administering the anti-fungal agent and cancer therapy prolongs the delay in tumor regrowth compared to non-treated tumors. In various other embodiments, the anti-fungal agent causes a decrease in a fungal population. In yet other embodiments, the anti-fungal agent is fluconazole, 5-flurocytosine and amphotericin B.

In various embodiments, the cancer therapy is radiation therapy (RT).

BRIEF DESCRIPTION OF THE FIGURES

Exemplary embodiments are illustrated in referenced figures. It is intended that the embodiments and figures disclosed herein are to be considered illustrative rather than restrictive.

FIG. 8A) Abx: Vancomycin, Imipenem/Cilastin, Ampicillin and Radiation Therapy: 12 Gy, upper mammary gland; FIG. 8B) Abx: vancomycin (500 mg/L), imipenem/cilastatin (500 mg/L) and neomycin (1 g/L) and Radiation Therapy: 16 Gy. Other combinations tested are 1) ampicillin (1 mg/ml), streptomycin (5 mg/ml), and colistin (1 mg/ml—Sigma-Aldrich) and 2) Vancomycin, Colistin and Ampicillin, data not shown.

FIG. 12A) Antifungal: Fluconazole; Radiation Therapy: 16 Gy. FIG. 12B) Treatment with a cocktail of antifungals caused a significantly enhanced reduction in tumor growth comparted with RT alone (n=10/group) (AF cocktail: fluconazole, 5-flurocytosine and amphotericin B). One of four representative experiments shown. **=p=0.01

FIG. 22A) For FACS, tumors were enzymatically dissociated with and labeled with fluorescently tagged antibodies and then placed on a flow cytometer. FIG. 22B) For IHC, tumor fragments were fixed in formalin and embedded in paraffin. 5 micron sections were then cut and stained with various antibodies and developed with DAB prior to whole-slide scanning on the Aperio system (Leica Biosystems). FIG. 22C) qPCR was performed on flow sorted immune cells (e.g. CD4+ T cells or macrophages) and then subjected to qPCR with a panel of primers.

FIG. 24A) Bacterial 16S sequencing. FIG. 24B) Fungi ITS sequencing. Fresh fecal pellets from mice treated with one week of a cocktail of antibiotics (vancomycin, neomycin, imipenem, cilastin) or antifungals (fluconazole, 5-fluorocytosine or amphotericin B) were collected. DNA was obtained and sequenced as previously described. (n=5 per group)

FIGS. 26A-26J depict that antifungals enhance and antibiotics diminish the tumor response to RT, in accordance with various embodiments of the invention. Orthotopic E0771 mammary tumors were grown to a median diameter of 1.0 cm and mice were then started with either antibiotics (Abx) or antifungals (AF) for one week prior to being treated with localized kV irradiation (16 Gy). Total tumor burden/animal assessed every 3 days until endpoint. Both individual tumors (FIG. 26A, FIG. 26B, FIG. 26D, FIG. 26E) and mean tumor burden±SEM (FIG. 26C, FIG. 26G) are displayed with their indicated treatment. Antibiotics (Abx) were ampicillin, imipenem, cilastin and vancomycin. Fluconazole was the antifungals (AF) used for these experiments. Significance was determined by two-way ANOVA. Kaplan-Meier survival curves are also shown with significance determined by the Log-Rank test (FIG. 26G, FIG. 26H). One of five experiments is shown. Tumors from mice were harvested at one week following RT and stained for bromodeoxyuridine (BrdU) and cleaved caspase 3 (CC3) to assess for proliferation and cell death respectively (FIG. 26I, FIG. 26J). Slides were scanned using the Aperio slide scanner and analyzed using the ScanScope nuclear algorithm included in the Aperio software package. Significance was determined by two-way ANOVA. For all figures significance is shown as *p<0.05, p<0.01, *p<0.001.

FIGS. 28A-28H depict the depletion of bacteria, but not fungi, decreases the anti-tumor immunity, in accordance with various embodiments of the invention. Irradiated E0771 mammary tumors were harvested from mice at one week following RT. Tumors were dissociated using the tumor dissociation kit (Miltenyi Biotech) and CD45+ cells were then isolated with CD45+ MacsBeads. The resulting CD45+ cells were then stained with fluorescent antibodies and run on a flow cytometer. Total leukocytes (CD45+ Cells), CD4+ T cells, CD8+ T cells, M1 macrophages (CD11b+Ly6C+) and M1 macrophages (CD11b+F4/80') were assessed following antibiotic (FIG. 28A-FIG. 28D) and antifungal (FIG. 28E-FIG. 28H) treatment. Antibiotics (Abx) were ampicillin, imipenem, cilastin and vancomycin. Fluconazole was the antifungal (AF) used for these experiments. n=5-7 per group and represent one of five independent experiments.

FIGS. 29A-29C depict antibiotic treatment leads to diminished fungal diversity, in accordance with various embodiments of the invention. Principal component analysis was done at the genus level using the R statistical package to identify differences between the bacterial (FIG. 29A) and fungal (FIG. 29B) populations in the untreated and treated groups. The alpha (Shannon) diversity was then calculated for both bacterial and fungal populations (FIG. 29E). Antibiotics (Abx) were ampicillin, imipenem, cilastin and vancomycin. Fluconazole was the antifungals (AF) used for these experiments. n=5-8 per group and represent one of five independent experiments.

DESCRIPTION OF THE INVENTION

Figure 1:
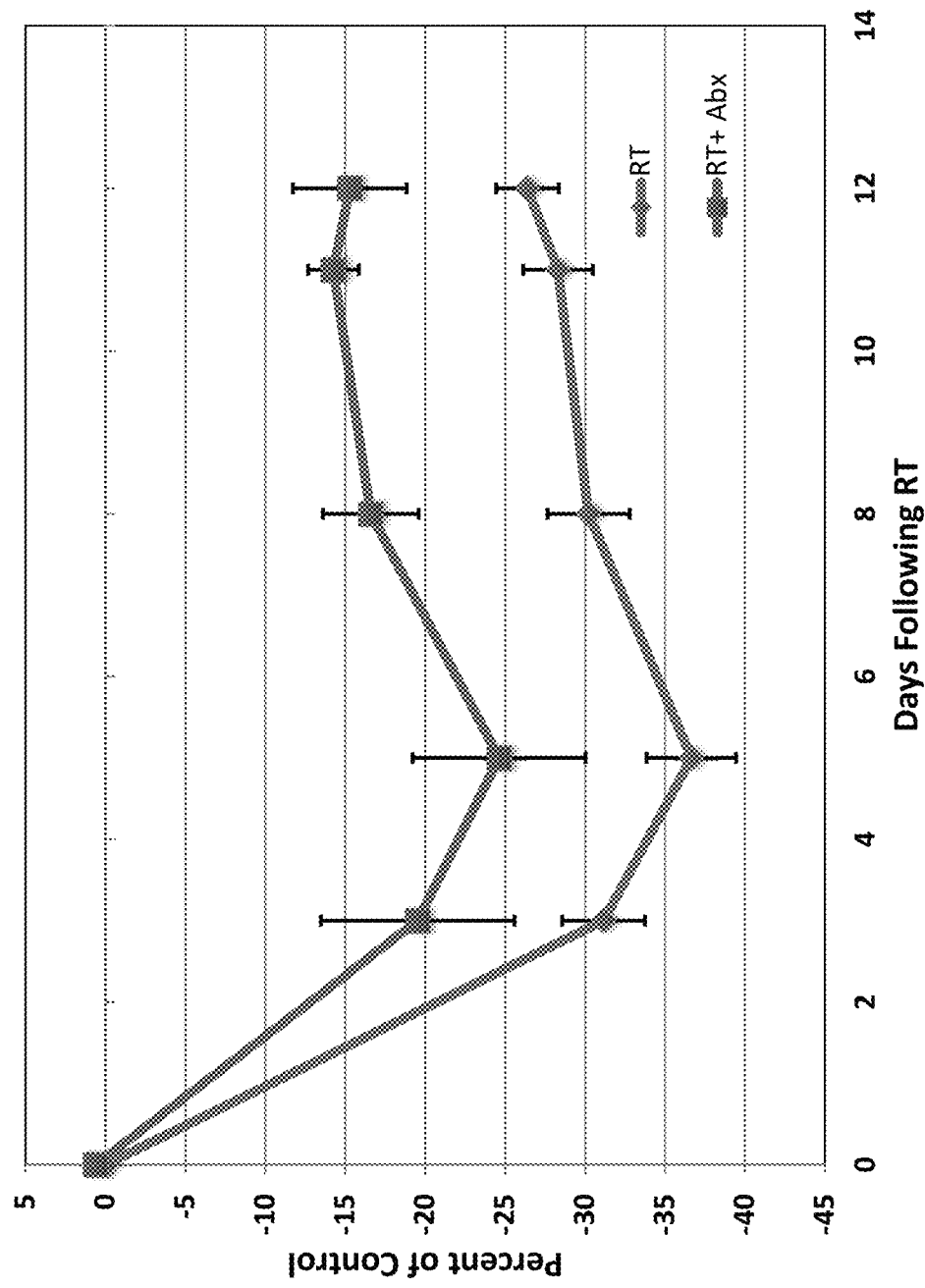
FIG. 1 depicts that antibiotic treatment reduces the efficacy of RT. Treatment with a four cocktail abx regimen (vancomycin (500 mg/L), streptomycin, ampicillin (1 g/L) and metronidazole) starting one week prior to irradiation shows significantly less reduction in tumor growth compared with RT alone (n=5/group). Radiation Therapy: 16 Gy.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"RT" as used herein is an abbreviation of radiation therapy.

"ABX" as used herein is an abbreviation of antibiotics.

"AF" as used herein is an abbreviation of antifungals.

"ASF" as used herein is an abbreviation of altered Schaedler flora.

"DC" as used herein is an abbreviation of dendritic cell.

"GF" as used herein is an abbreviation of germ-free.

"Gy" as used herein is an abbreviation of Gray.

"SPF" as used herein is an abbreviation of specific-pathogen free.

"TLR" as used herein is an abbreviation of Toll-like receptor.

"IFN" as used herein is an abbreviation of interferon gamma.

"Antifungal Agent" as used herein refers to an agent that can suppress, at least partially eradicate or eradicate a fungal organism.

"Cancer therapy" as used herein refers to a therapeutic treatment for cancer. Examples of cancer therapies include, but are not limited to, radiation therapy, chemotherapy, immunotherapy and targeted therapy. A targeted therapy can comprise a drug combination that more precisely identifies and attacks cancer cells, for example, by targeting genes and/or signaling pathways that drive the cancer/tumor.

The terms "cancer" and "cancerous" refer to or describe the physiological condition in mammals that is typically characterized by unregulated cell growth. Included in this definition are malignant cancers as well as dormant tumors or micrometastatses. Examples of cancer include, but are not limited to, brain, lung, liver, and/or breast cancer. The cancer may be newly diagnosed, diagnosed, or recurrent.

"Tumor," as used herein refers to all neoplastic cell growth and proliferation, whether malignant or benign, and all pre-cancerous and cancerous cells and tissues.

A "recurrence" with respect to cancer means that the cancer has returned after initial treatment. Being recurrent means that the cancer is growing and/or has metastasized and treatment is required to lower the chance of lethality.

Being "non-recurrent" or "recurrence-free" means that the cancer is in remission.

Terms such as "treating" or "treatment" or "to treat" or "alleviating" or "to alleviate" refer to therapeutic treatment and/or prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. Thus, those in need of treatment include those already with the disorder; those prone to have the disorder; and those in whom the disorder is to be prevented.

The term "subject" refers to any animal (e.g., a mammal), including, but not limited to humans, non-human primates, rodents, and domestic and game animals, which is to be the recipient of a particular treatment. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf. Typically, the terms "subject" and "patient" are used interchangeably herein in reference to a human subject. In various embodiments, a subject can be one who has been previously diagnosed with or identified as suffering from or having a condition in need of treatment. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits one or more risk factors for a condition). A "subject in need" of treatment for a particular condition can be a subject having that condition, diagnosed as having that condition, or at risk of developing that condition.

The term "therapeutically effective amount" refers to an amount of an antifungal, fungal probiotic, antibody, antibiotic, polypeptide, polynucleotide, small organic molecule, or other drug effective to "treat" a disease or disorder in a subject or mammal. In the case of cancer, the therapeutically effective amount of the composition that modulates a fungal population can increase or decrease the fungal population. The therapeutically effective amount of the composition that modulates a fungal population in addition to a cancer therapy enhances the therapeutic response of the cancer therapy to treat cancer. In some embodiments, the fungal probiotic administered comprises *Wallemia, Epicoccum* and/or *Aspergillus*. In yet other embodiments, the fungal probiotic administered comprising *Wallemia, Epicoccum* and/or *Aspergillus* enhances the cancer therapy.

In various embodiments, the therapeutically effective amount of the composition that modulates a fungal population, The invention is based, at least in part, on the identification that targeting and/or modulating fungal populations in addition to cancer therapies enhances the anti-tumor response.

The Role of Inflammation in Breast Cancer

While breast cancer has not historically been linked to underlying inflammation or infection, it exhibits tumor-associated inflammation marked by infiltration of leukocytes into developing tumors where increases in innate and adaptive leukocytes in neoplastic stroma parallels disease progression. While genetic and epigenetic changes in genes that regulate mammary epithelial cell (MEC) proliferation, survival and/or differentiation are likely 'initiators' of breast cancer, there is emerging evidence to indicate that stromal cell responses including leukocyte recruitment into premalignant mammary tissue 'promote' progression to cancer and/or foster metastatic capability of malignant MECs. Retrospective clinical studies examining immune responses in human breast cancer have found that high immunoglobulin (Ig) levels in tumor stroma (and serum), high ratios of CD4/CD8 or TH2/TH1 T cells in tumors correlate with tumor grade, stage and overall survival. Classically, TH1 microenvironments driven by IFNγ and IL-12 have been considered anti-tumor, while TH2 microenvironments driven by IL-4 have been identified as pro-tumorigenic. The ability to identify and correlate the presence of different immune cells within the tumor with prognosis suggests that the nature of the immune microenvironment is a critical determinant in breast cancer progression. However, little is known about the effect of the type of microenvironment in the response to cytotoxic therapies such as chemotherapy or RT nor how it may be altered by changes in the microbiome communities.

Microbiome-Regulation of Systemic Immune Responses

The commensal microbiota influences metabolism, tissue development, inflammation, and immunity. The gut microbiota affects inflammation and immunity not only within the gut itself but also systemically. Recent experimental data from several groups has revealed that the microbiome affects inflammatory processes that contribute to cancer development and the efficacy of cancer therapy. Using mouse models of cancer they demonstrated that the efficacy of immunotherapy (CpG oligonucleotides) and more traditional cytotoxic chemotherapies including oxaliplatin and cyclophosphamide have markedly reduced efficacy when mice were treated with antibiotics that deplete the bacterial gut microflora as a result of an attenuated anti-tumor immune response. This raised the question of whether or not antibiotic treatment would similarly reduce the efficacy of RT. Recent work from the inventor's lab demonstrated for the first time that fungi also play a critical role in regulating the inflammatory status of the intestine. Without being bound to any particular theory, we believe that fungi play a role in regulating the response to chemotherapy and RT.

Regulation of the Response to Radiation Therapy by the Immune System

Cytotoxic therapies such as chemotherapy and RT have historically been seen as immunosuppressive and the current rationale for their use is largely predicated on the ability of these modalities to kill cancer cells by a direct cytotoxic effect. However, recent data from the Zitvogel group and others have demonstrated a connection between immune activation and the effectiveness of both RT and chemotherapy. Through genetic analyses evidence was found that mutations in toll-like receptor 4 (TLR4), a key receptor in activation of innate immunity, are predictive for anthracycline resistance. Then several mouse models of cancer were used to demonstrate that interactions between TLR4 and its ligand influence the effectiveness of RT and some but not all chemotherapeutics due to the differential potential of specific chemotherapeutic agents to release pro-inflammatory mediators from dying tumor cells. Multiple other mechanisms have since been identified by which different chemotherapies and RT can kill tumor cells in ways that activate the immune system. The idea that RT can influence the systemic immune response has also been further demonstrated in a model of murine mammary carcinogenesis where syngeneic tumor cells were implanted into mice at two different locations. Irradiation of one tumor site resulted in inhibition of tumor growth at the other, non-irradiated site in a T cell and dendritic cell (DC)-dependent manner. Furthermore, there is evidence that chemotherapy and RT influence tumor antigen presentation, immune cell homing to tumors and production of pro-inflammatory molecular signals. Without being bound to any particular theory, these data all indicate that chemotherapy and RT may regulate immune responsiveness to tumors by altering the tumor microenvironment to favor presentation and stimulation of tumor-specific T cells. The microbiome can affect all of these aspects of immune function and, without being bound to any particular theory, data identifying new approaches incorporating novel immune-based therapeutics along with chemotherapy and/or RT aid in enhancing patient survival in breast cancer.

The general paucity of information on the immune response following RT, the evidence of the role of immunity in the anti-tumor effects of RT, and the recent characterization of the microbiome as a key immune regulator come together to make this a compelling time to develop model systems for defining how the microbiome and the immune system interact with tumors following RT. There are very few studies currently focusing on the role of the host immune system following RT despite compelling need for such investigations. There are no studies that have explored how alterations in the microbiome might affect the response to RT or how targeting/modulating the microbiome can influence breast cancer. The orthotopic mouse model used in the study described herein provides a novel and logical model for investigating this. In addition, the advent of multiplex flow cytometry and immunohistochemical techniques has made possible the characterization of the complex immune landscape. Very few studies to date have applied this technology to the immune profile of tumors and none have utilized this technique following RT or chemotherapy treatment of tumors.

Interest in the role of the microbiome in regulating systemic immune responses has increased and recent data has revealed a critical role for the microbiome in many disease states including autoimmunity and tumor responses to chemotherapy. RT and chemotherapy remain the standard of care for patients diagnosed with breast cancer, however despite recent gains many women still fail treatment eventually succumbing to this disease. Part of this treatment failure may be due to the inability to generate a productive immune response to cell death induced by chemotherapy and RT. Since the microbiome shapes the nature of immune responses in many other disease states, without being bound to any particular theory, we believe that efficacy and durability of RT will be changed following depletion of the microbiome through a reduction in the TH1-type immune bioactivity following treatment. The preclinical models used herein have been extensively validated and thus can be readily translated to the clinic for evaluation.

Without being bound to any particular theory, targeting/modulating fungal populations in addition to cancer therapies such as radiation, chemotherapy and targeted therapies enhances the anti-tumor response. While fungal agents and, of course, cancer therapeutics have been around for decades, the idea that using agents that target fungi (and components of the fungal microbiome) can affect the efficacy of cancer treatments including radiation, chemotherapy, target agents and immunotherapy has not been done. The bacterial microbiome has been recently described to affect the response to chemotherapy and immunotherapy, but has never been described to affect the efficacy of radiation. While many patients with cancer respond to radiation and chemotherapy, many patients do not respond and others do not have durable responses. This invention modulates the fungal microbiome to enhance the response to these therapies in cancer. Current treatments for cancer (chemotherapy, radiation, targeted therapies and immunotherapies) are used in combinations to enhance the anti-tumor response, however there are currently no solutions to enhance these treatments and none that are approved that target the immune system/microbiome. There are many combination therapies in cancer treatment, but none so far have specifically targeted the fungal microbiome to enhance the efficacy of cancer therapy.

The present invention is based, at least in part, on these findings. The present invention addresses the need in the art for a treatment strategy that enhances the efficacy of cancer therapies. The invention provides the combination of treating a subject by targeting/modulating the fungal population in addition to cancer therapy. Methods of treating using the combination are further provided.

Methods of Treatment

Various embodiments of the present invention provide for a method of treating cancer or reducing tumor size in a subject in need thereof, comprising administering a therapeutically effective amount of a composition that modulates a fungal population and administering a therapeutically effective amount of a cancer therapy. In various embodiments, the cancer is breast cancer.

In various embodiments, the administration of the composition modulates a fungal population and enhances the therapeutic response to the cancer therapy. In various other embodiments, the administration of the composition modulates a fungal population and enhances the anti-tumor response to the cancer therapy.

In various embodiments, the composition that modulates the fungal population is an anti-fungal agent and/or a fungal probiotic. In various other embodiments, the anti-fungal agent causes a decrease in the fungal population. In other embodiments, the fungal populations decreased are *Aspergillus, Cladosporium, Phoma, Guehomyces, Candida tropicalis* or combinations thereof. In yet other embodiments, the anti-fungal agent is fluconazole, 5-flurocytosine, amphotericin B or a combination thereof.

In various embodiments, the fungal probiotic causes an increase in the fungal population. In various other embodiments, the fungal populations increased are *Wallemia, Epicoccum, Apergillus, Apergillus amstelodami, Saccharomyces cerevisiae* or combinations thereof.

In various embodiments, the cancer therapy is radiation therapy, chemotherapy, immunotherapy and/or targeted therapy. In various embodiments, the cancer therapy is radiation therapy (RT). In various embodiments, RT is administered in a dosage between 2 Gy to 34 Gy. In yet other embodiments, the RT is administered for 1 to 7 weeks.

In various embodiments, the method further comprises administering a therapeutically effective amount of an antibiotic, and the antibiotic is not a combination of vancomycin, streptomycin, ampicillin, and metronidazole, is not vancomycin, colistin, and ampicillin, is not vancomycin, imipenem/cilastin, and streptomycin, is not vancomycin, imipenem/cilastin, and ampicillin, is not ampicillin, streptomycin, and colistin, or is not vancomycin, imipenem/cilastatin, and neomycin, if the cancer therapy is RT.

Various embodiments of the present invention also provide for a method of enhancing the efficacy of a cancer therapy in a subject in need thereof, comprising administering a therapeutically effective amount of an anti-fungal agent and administering a therapeutically effective amount of a cancer therapy. In various embodiments, the subject is a subject with breast cancer.

In various embodiments, administering the anti-fungal agent and cancer therapy prolongs the delay in tumor regrowth compared to non-treated tumors. In various other embodiments, the anti-fungal agent causes a decrease in a fungal population. In yet other embodiments, the anti-fungal agent is fluconazole, 5-flurocytosine and amphotericin B.

In various embodiments, the cancer therapy is radiation therapy (RT). In various other embodiments, the RT is administered in a single dose of 12 Gy.

Various embodiments of the present invention also provide for a method of treating cancer in a subject in need thereof, comprising administering a therapeutically effective amount of a composition that modulates a fungal population and a cancer therapy.

In various embodiments, the cancer is breast cancer. In various embodiments, the administration of the composition that modulates a fungal population and enhances the therapeutic response of the cancer therapy. In various other embodiments, the administration of the composition that modulates a fungal population and the cancer therapy enhances the anti-tumor response. In yet other embodiments, the composition that modulates the fungal population is an anti-fungal agent and/or a fungal probiotic.

In various embodiments, the anti-fungal agent causes a decrease in the fungal population. In other embodiments, the anti-fungal agent is fluconazole. In various other embodiments, the fungal probiotic causes an increase in the fungal population.

In various embodiments, the cancer therapy is radiation therapy, chemotherapy, immunotherapy and/or targeted therapy. In other embodiments, the cancer therapy is radiation therapy. In various embodiments, the method further comprises administering a therapeutically effective amount of an antibiotic.

Various other embodiment of the present invention also provide for a method of reducing tumor size in a subject in need thereof, comprising: administering a therapeutically effective amount of a composition that modulates a fungal population and a cancer therapy.

In various embodiments, the cancer is breast cancer. In various other embodiments, the administration of the composition that modulates a fungal population, enhances the therapeutic response of the cancer therapy. In yet other embodiments, the administration of the composition that modulates a fungal population and the cancer therapy enhances the anti-tumor response. In various embodiments, the composition that modulates the fungal population is an anti-fungal agent and/or a fungal probiotic. In other embodiments, the anti-fungal agent causes a decrease in the fungal population. In yet other embodiments, the anti-fungal agent is fluconazole. In various embodiments, the fungal probiotic causes an increase in the fungal population. In other embodiments, the cancer therapy is radiation therapy, chemotherapy, immunotherapy and/or targeted therapy. In yet other embodiments, the cancer therapy is radiation therapy.

In various embodiments, the method further comprising administering a therapeutically effective amount of an antibiotic.

In certain embodiments, the disease treated is cancer. The cancer may be newly diagnosed, recurrent or non-recurrent. In other embodiments, the cancer is brain, lung, liver and/or breast cancer. In some embodiments, the cancer is a mammary tumor. In other embodiments, the tumor is an adenocarcinoma. In some other embodiments, the cancer is breast cancer.

In various other embodiments, the administration of the composition that modulates a fungal population enhances the therapeutic response of the cancer therapy. In yet other embodiments, the administration of the composition that modulates a fungal population and the cancer therapy, enhances the anti-tumor response. In various embodiments, the composition that modulates the fungal population is an anti-fungal agent and/or a fungal probiotic. In various embodiments, the anti-fungal agent causes a decrease in the fungal population. In various other embodiments, the anti-fungal agent is fluconazole. In some embodiments, the fungal populations decreased, following the administration of an anti-fungal agent, comprise *Aspergillus, Cladosporium, Phoma* and/or *Guehomyces*. In yet other embodiments, the fungal probiotic causes an increase in the fungal population. In some embodiments, the fungal populations increased, following the administration of the fungal probiotic, comprise *Wallemia, Epicoccum* and/or *Aspergillus*.

In various embodiments, enhanced efficacy to RT in antifungal treated mice results from either a rise in *Aspergillus amstelodami* or a reduction in *Candida tropicalis*. In various other embodiments, reduced efficacy of RT in antibiotic-treated mice could arise from the increase in *Saccharomyces cerevisiae* populations in the gut. In yet other embodiments, the fungal population increased is *Aspergillus amstelodami*, following the administration of the fungal probiotic. In other embodiments, the fungal population decreased is *Candida tropicalis*, following the administration of the antifungal. In various other embodiments, the fungal population decreased is *Saccharomyces cerevisiae*, following the administration of an antifungal.

In various embodiments, the cancer therapy is radiation therapy, chemotherapy, immunotherapy and/or targeted therapy. In various other embodiments, the cancer therapy is radiation therapy. In some embodiments, the subject is receiving or is a candidate to receive cancer therapy.

In various other embodiments, the method further comprises administering a therapeutically effective amount of an antibiotic. In some embodiments, the antibiotic administered causes a modulation in the bacterial population. In various embodiments, the modulation of the bacterial population alters the efficacy of the cancer therapy. In some embodiments, the modulation of the bacterial population increases the efficacy of the cancer therapy. In various embodiments, the antibiotics are administered as a combination of antibiotics. In some embodiments, the antibiotic and RT are administered. In other embodiments, the combination of antibiotics and RT are administered. In various embodiments, the antibiotic combination is not a combination of vancomycin, streptomycin, ampicillin, and metronidazole, when administered with RT. In other embodiments, the antibiotic combination is not a combination of vancomycin, colistin, and ampicillin, when administered with RT. In some other embodiments, the antibiotic combination is not a combination of vancomycin, imipenem/cilastin, and streptomycin, when administered with RT. In yet other embodiments, the antibiotic combination is not a combination of vancomycin, imipenem/cilastin, and ampicillin, when administered with RT. In some embodiments, the antibiotic combination is not a combination of ampicillin, streptomycin, and colistin, when administered with RT. In some other embodiments, the antibiotic combination is not a combination of vancomycin, imipenem/cilastatin, and neomycin, when administered with RT.

Route of Administration and Dosages

Various embodiments of the present invention provide for the administration of a therapeutically effective amount of a composition that modulates a fungal population and a cancer therapy, as part of a treatment strategy that aids in the treatment of cancer. In some embodiments, the composition that modulates a fungal population is an anti-fungal. Examples of antifungal agents include, but are not limited to, Imidazoles: Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole; Triazoles: Albaconazole, Efinaconazole, Epoxiconazole, Fluconazole, Isavuconazole, Itraconazole, Posaconazole, Propiconazole, Ravuconazole, Terconazole, Voriconazole; Thiazoles: Abafungin; Allylamines: Amorolfin, Butenafine, Naftifine, and Terbinafine; Echinocandins: Anidulafungin, Caspofungin, Micafungin; Polyene antifungals: amphotericin, nystatin and other agents such as, Benzoic acid, Ciclopirox—(ciclopirox olamine), Flucytosine or 5-fluorocytosine, Griseofulvin, Haloprogin, Tolnaftate, Undecylenic acid, Crystal violet, and Balsam of Peru. In various embodiments, the anti-fungal agent causes a decrease in the fungal population. In various embodiments, the anti-fungal agent in combination with a cancer therapy enhances the therapeutic response of the cancer therapy. In various embodiments, the cancer therapy is radiation therapy. In various embodiments, the anti-fungal agent is administered in combination with radiation therapy. In various embodiments, the antifungal and cancer therapy are administered simultaneously. In various embodiments, the antifungal and cancer therapy are administered sequentially. In various other embodiments, the antifungal is administered prior to cancer therapy administration. In various embodiments, the antifungal can be administered 1-4 hours, 4-8 hours, 8-12 hours, 12-16 hours, 16-20 hours or 20-24 hours prior to cancer therapy administration. In various embodiments, the antifungal can be administered 1 day, 2 days, 3 days, 4 days, 5 days or 6 days prior to cancer therapy administration. In various embodiments, the antifungal can be administered 1 week, 2 weeks, 3 weeks or a month prior to cancer therapy administration. In various embodiments, the antifungal is administered 1 week prior to cancer therapy administration. In various other embodiments, the anti-fungal agent is fluconazole, 5FC, and/or Amphotericin B. In various other embodiments, the anti-fungal agent is the combination of fluconazole, 5FC, and Amphotericin B. In various other embodiments, the anti-fungal agent is fluconazole. In various other embodiments, fluconazole and radiation therapy are administered to enhance the therapeutic response of a cancer therapy to treat cancer. In yet other embodiments, fluconazole and radiation therapy are administered to enhance the therapeutic response of the cancer therapy to treat breast cancer. In various other embodiments, the combination of fluconazole, 5FC, and Amphotericin B and radiation therapy are administered to enhance the therapeutic response of a cancer therapy to treat cancer. In yet other embodiments, the combination of fluconazole, 5FC, and Amphotericin B and radiation therapy are administered to enhance the therapeutic response of the cancer therapy to treat breast cancer. In other embodiments, the composition that modulates a fungal population is a fungal probiotic.

In various embodiments, the composition that modulates a fungal population may be formulated for delivery via any route of administration. "Route of administration" may refer to any administration pathway known in the art, including but not limited to aerosol, nasal, oral, transmucosal, transdermal or parenteral.

"Transdermal" administration may be accomplished using a topical cream or ointment or by means of a transdermal patch.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they may be in the form of eye drops.

In various embodiments, the composition that modulates a fungal population can be administered intravenously by injection or by gradual infusion over time. Given an appropriate formulation for a given route, for example, the composition that modulates a fungal population can be administered intravenously, intranasally, by inhalation, intraperitoneally, intramuscularly, subcutaneously, intracavity, and can be delivered by peristaltic means, if desired, or by other means known by those skilled in the art. It is preferred that the composition that modulates a fungal population is administered orally, intravenously or intramuscularly to a patient having cancer, in particular brain cancer.

The composition that modulates a fungal population according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, the present invention provides a composition that modulates a fungal population which includes a pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in the therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. The composition that modulates a fungal population as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent used in the invention that will be effective in the treatment of a particular disorder or condition will depend on the nature of the disorder or condition, and can be determined by one of skill in the art with standard clinical techniques.

The composition that modulates a fungal population according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapy/therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of the composition that modulates a fungal population can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biological samples obtained, or the responses observed in the appropriate animal models.

For the treatment of the disease, the appropriate dosage of the composition that modulates a fungal population depends on the type of disease to be treated, the severity and course of the disease, the responsiveness of the disease, whether the therapy is administered for therapeutic or preventative purposes, previous treatment, and the patient's clinical history. The dosage can also be adjusted by the individual physician in the event of any complication and at the discretion of the treating physician. The administering physician can easily determine optimum dosages, dosing methodologies and repetition rates. The administering physician can determine optimum dosages, dosing methodologies and repetition rates.

The composition that modulates a fungal population can be administered one time or over a series of treatments lasting from several days to several months, or until a cure is effected or a diminution of the disease state is achieved (e.g., treatment or amelioration of cancer). The duration of treatment depends upon the subject's clinical progress and responsiveness to therapy. In certain embodiments, dosage is from 0.01 μg to 100 mg per kg of body weight, and can be given once or more daily, weekly, monthly or yearly. For systemic administration, subjects can be administered a therapeutic amount, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. In other embodiments, the composition that modulates a fungal population is a fungal probiotic. In some embodiments, the fungal probiotic can be administered one time or over a series of treatments lasting from several days to several months, or until a cure is effected or a diminution of the disease state is achieved (e.g., treatment or amelioration of cancer). The duration of treatment depends upon the subject's clinical progress and responsiveness to therapy. In certain embodiments, the dosage of the fungal probiotic is in the range of about $10^1$ to about $10^{13}$ cells or colony-forming units (CFUs). The dosage of the fungal probiotic administered to the subject can range from about $10^1$-$10^2$ cells or CFUs, $10^2$-$10^4$ cells or CFUs, $10^4$-$10^6$ cells or CFUs, $10^6$-$10^8$ cells or CFUs, $10^8$-$10^{10}$ cells or CFUs, $10^{10}$-$10^{13}$ cells or CFUs.

In various embodiments of the present invention, the composition that modulates a fungal population is administered in the subject for treatment. In various other embodiments, the composition that modulates a fungal population is administered in a series of treatments. In various embodiments, the composition that modulates a fungal population is administered with a cancer therapy in the subject for treatment. In some embodiments, the composition that modulates a fungal population and the cancer therapy may be administered in any order or concurrently. In selected embodiments, the composition that modulates a fungal population and the cancer therapy will be administered to patients that have previously undergone treatment. In certain other embodiments, the composition that modulates a fungal population and the cancer therapy will be administered substantially simultaneously or concurrently. For example, a subject may be given the composition that modulates a fungal population while undergoing a course of treatment with a cancer therapy. In certain embodiments, the composition that modulates a fungal population will be administered within 1 year of the treatment with the cancer therapy. In certain alternative embodiments, the composition that modulates a fungal population will be administered within 10, 8, 6, 4, or 2 months of any treatment with a cancer therapy. In certain other embodiments, the composition that modulates a fungal population will be administered within 4, 3, 2, or 1 week of any treatment with the cancer therapy. In some embodiments, the composition that modulates a fungal population will be administered within 5, 4, 3, 2, or 1 days of any treatment with a cancer therapy. It will further be appreciated that the two treatments may be administered to the subject within a matter of hours or minutes (i.e., simultaneously). Treatment with the composition that modulates a fungal population can occur prior to, concurrently with, or subsequent to administration of a cancer therapy. Combined administration can include co-administration, either in a single pharmaceutical formulation or using separate formulations, or consecutive administration in either order but generally within a time period such that all active agents can exert their biological activities simultaneously. Any dosing schedules for the composition that modulates a fungal population and/or the cancer therapy can also be used as determined by the skilled practitioner.

In some embodiments, the cancer therapy is radiation therapy, chemotherapy, immunotherapy and/or targeted therapy. Examples of a chemotherapeutic include, but are not limited to, Bevacizumab, Carmustine, Carmustine, Lomustine, Everolimus, Temozolomide, Taxotere, pemetrexed, Cabazitaxel, Estramustine, Docetaxel, Paclitaxel, Platinum agents (cisplatin, carboplatin), Vinorelbine, Capecitabine, Liposomal doxorubicin, Gemcitabine, Mitoxantrone, cyclophosphamide, Doxorubicin, and Vincristine. Examples of an immunotherapy, include, but are not limited to, check point inhibitors and/or dendritic cell vaccines.

In various embodiments, the cancer therapy is radiation therapy. Radiation therapy uses high-energy radiation, such as, x-rays, gamma rays, and charged particles, to shrink tumors and kill cancer cells. Examples of radiation therapy include, but are not limited to, external-beam radiation therapy, internal radiation therapy (brachytherapy) or systemic radiation therapy (radioactive substances, such as radioactive iodine). Targeted therapies are drugs or other substances designed to block the growth and spread of cancer by preventing cancer cells from dividing or by destroying them directly. The drugs or other substances target specific molecules that are responsible for the growth, progression and spread of cancer. Examples of targeted therapy include, but are not limited to, hormone therapies, signal transduction inhibitors, gene expression modulators, apoptosis inducers, angiogenesis inhibitors and monoclonal antibodies that deliver toxic molecules.

The duration of the treatment can be continued for as long as medically indicated or until a desired therapeutic effect (e.g., those described herein) is achieved. In certain embodiments, the therapy is continued for 1 month, 2 months, 4 months, 6 months, 8 months, 10 months, 1 year, 2 years, 3 years, 4 years, 5 years, or for a period of years up to the lifetime of the subject. The duration of treatment and type of treatment depends upon the subject's clinical progress, and responsiveness to therapy. In certain embodiments, dosage is from 0.01 µg to 100 mg per kg of body weight, and can be given once or more daily, weekly, monthly or yearly. The progress of the therapy administered is easily monitored by conventional techniques and assays.

In various embodiments, the RT dose can range from about 8-20 Gy. In various other embodiments, the RT dose can range from 8-10 Gy, 10-12 Gy, 12-14 Gy, 14-16 Gy, 16-18 Gy or 18-20 Gy. In various embodiments, the dose of a single RT administration can be 2 Gy for a low dose, 16 Gy for a medium dose or 34 Gy for a high dose. In various embodiments, the dose of a single RT administration is 12 Gy.

In various embodiments, the RT is delivered over multiple daily fractions (fractionated RT). For example, a low dose fractionated administration schedule may comprise a fraction size (radiation dose) of 2 Gy, with 5 fractions administered over a period of time. In various embodiments, the fraction size can range from about 2-34 Gy. In various other embodiments, the fraction size can range from 2-4 Gy, 4-6 Gy, 6-8 Gy, 8-10 Gy, 10-12 Gy, 12-14 Gy, 14-16 Gy, 16-18 Gy, 18-20 Gy, 20-22 Gy, 22-24Gy, 24-26 Gy, 26-28 Gy, 28-30 Gy, 30-32 Gy or 32-34 Gy. In some embodiments, the fraction size is 2 Gy for a low dose, 4 Gy for a medium dose or 8 Gy for a high dose. The number of fractions administered can range from about 1-2 fractions, 2-3 fractions, 3-4 fractions, 4-5 fractions, 5-6 fractions, 6-7 fractions, 7-8 fractions, 8-9 fractions or 9-10 fractions. In some embodiments, the duration of fractionated RT administration ranges from about 1 week to 7 weeks or more.

Preparation and dosing schedules for the administration of chemotherapeutic agents, immunotherapeutic agents, radiation therapy and targeted therapeutic drug combinations may be used according to manufacturer's instructions or as determined empirically by the skilled practitioner.

Kits

The present invention is also directed to a kit to treat cancer, in particular brain, lung, liver and/or breast cancer. The kit comprises the composition that modulates a fungal population, which can be used to perform the methods described herein. In various embodiments, the composition that modulates a fungal population is an anti-fungal agent. In various embodiments, the anti-fungal agent is fluconazole. In various embodiments, the composition that modulates a fungal population is a fungal probiotic. The kit is useful for practicing the inventive method of providing treatment to a cancer patient by administering the composition that modulates a fungal population. In various other embodiments, the composition that modulates a fungal population is administered in combination with a cancer therapy. The kit is an assemblage of materials or components, including at least one of the inventive compositions. Thus, in some embodiments the kit contains a composition that modulates a fungal population, for the treatment of cancer, as described above.

The exact nature of the components configured in the inventive kit depends on its intended purpose. For example, some embodiments are configured for the purpose of treating cancer. In other embodiments, the kit is configured for the purpose of treating brain, lung, liver and/or breast cancer. In other embodiments, the kit is configured for the purpose of treating breast cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or alleviate cancer in the subject. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in the administration of treatments. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing the composition that modulates a fungal population. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

PyMT Model and M2 Polarization in Breast Cancer

The MMTV-PyMT mouse model of mammary carcinogenesis is a model in which the mouse mammary tumor virus (MMTV) regulates expression of the polyoma middle T oncogene (PyMT) eliciting multi-stage neoplastic progression to adenocarcinoma that readily metastasizes to lung and genetically mimics the human luminal subtype of breast cancer. Moreover, the profile of leukocytes that infiltrate mammary adenocarcinomas in PyMT mice mirrors that found in human breast cancers as evaluated histologically or by polychromatic flow cytometry. Previous studies in PyMT mice revealed that TH2-CD4+ T cells regulate the formation of metastasis by enhancing the pro-tumor bioactivities of macrophages. Thus, the behavior of tumors in this model is subject to immune regulation leading us to believe, without being bound to any particular theory, that targeting/modulating the microbiome following RT with antibiotics, antifungal agents or supplementation with different bacteria or fungi will influence the response to RT.

Transplantation Model of Breast Cancer

Use of genetically engineered mouse models (GEMM) of mammary carcinogenesis such as the PyMT model is hampered by significant primary tumor burden in all mammary glands. Thus, to evaluate the efficacy of RT in setting of RT, a transplantation strategy that circumvents these issues was developed. Tumor fragments from PyMT mice are harvested and transplanted into the mammary fat pad on the thorax of naïve syngeneic mice to avoid irradiating the intestines, and tumor development monitored until palpable tumors appear and achieve a size of 1.0 cm. Tumor-bearing mice are then randomized and enrolled into treatment groups where primary tumor growth is monitored with and without antibiotics/antifungals and with and without RT prospectively to the study end-point. Primary tumors and metastases to lung, brain and liver are then evaluated histopathologically in tissue sections.

Microbiome Depletion with Antibiotics

Multiple antibiotic regimens have been described to deplete the bacterial flora of the gut. Using a combination of the vancomycin, neomycin, metronidazole and ampicillin administered in the drinking water, multiple investigators including our own laboratory have treated mice to deplete >99% of all bacteria in the gut. Depletion of gut fungi is done similarly with the addition of the antifungal agent fluconazole in the drinking water as we have previously described (Iliev, I. D., et al. Science 336, 1314-1317 (2012)).

Microbiome Depletion Reduces Efficacy of Chemotherapy and RT

Pilot studies using the orthotopic syngeneic transplantation model were conducted, to address the hypothesis that eliminating the microbiome would reduce the response to chemotherapy and/or RT. In these studies, primary tumor growth was limited by RT (12 Gy, single-fraction; FIG. 1). Tumor growth in mice given a four cocktail antibiotic (vancomycin, neomycin, metronidazole and ampicillin) plus RT evidenced significantly reduced responses as demonstrated by increased tumor growth to the study end-point (Square, FIG. 1). Without being bound to any particular theory, these data indicate that reprogramming immune microenvironments by targeting/modulating the microbiome, alters the survival of breast cancer patients by altering RT sensitivity. Furthermore, without being bound to any particular theory, depending on the baseline microbiome composition for a given patient, certain antibiotic sensitive bacteria may impact the efficacy of RT and chemotherapy.

Example 2

Recent studies in mice and humans have demonstrated that the phenotype of infiltrating leukocytes following treatment plays a significant role in determining disease progression. Without being bound to any particular theory, we believe that alterations in the composition of the microbiome will either enhance or diminish the efficacy of RT by influencing anti-tumor immunity to promote or reduce primary breast cancer development. To address this, the composition and activation state of immune cells in mammary tumors treated with focal RT are evaluated, in combination with depletion of specific components of the microbiome using antibiotics or antifungal agents targeting/modulating specific classes of bacteria or fungi. This reveals which immune cell types and stages of breast cancer development are influenced by treatment-induced changes. The mechanism of these changes is explored in vivo by selectively impairing discrete components of the immune response to understand which components are required for RT-induced effects in the presence of microbiome alterations.

Statistical Analysis

Based on our data, we performed a power calculation for the tumor size and quantitative immunohistochemistry. To analyze the differences in immune populations, quantities of the immune cells determined by flow cytometry or immunohistochemistry are transformed to approximate the normal distribution. Using 10 mice per group a one-way ANOVA at a significance level of 5% will provide 80% power to detect a 20% difference between group means assuming a standard deviation in tumor size and immune cell numbers of 25%. We also examine how other combinations of immune markers including T cells, cytokine expression and T cell phenotype are correlated by analysis of covariance and factor analysis. Ongoing statistical support will be provided by the Cedars-Sinai Biostatistics and Bioinformatics Core (Andre Rogatko, PhD).

Example 3

Figure 8B:
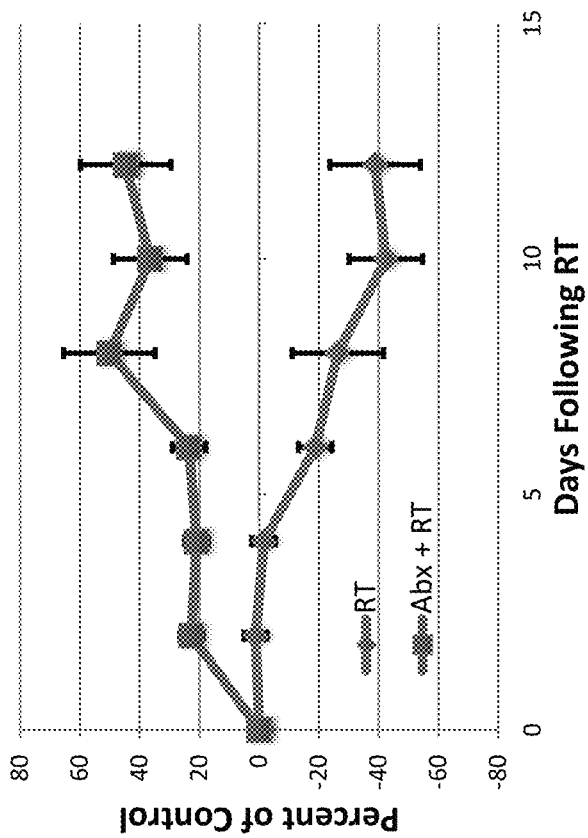
FIGS. 8A-8B depict antibiotic treatment reduces the efficacy of RT at different doses of RT.
Figure 8A:
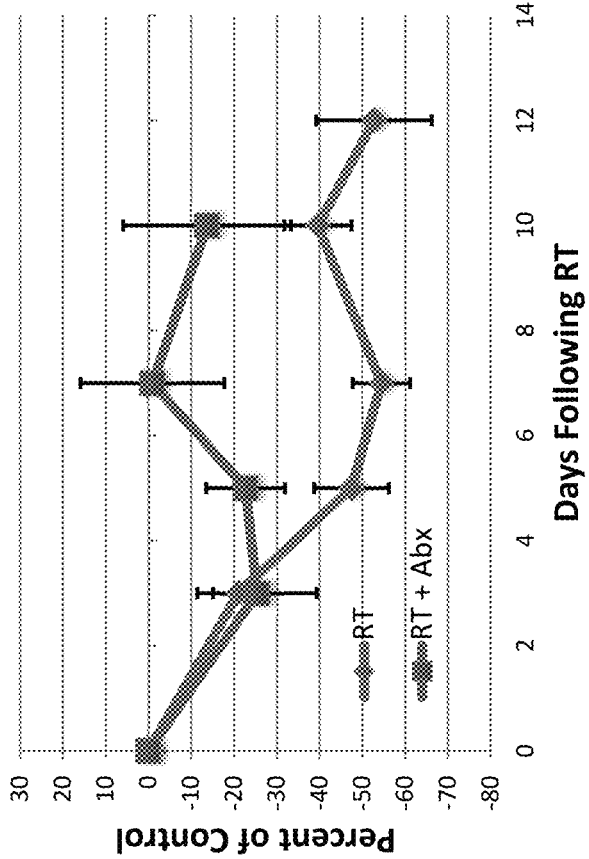
Figure 12A:
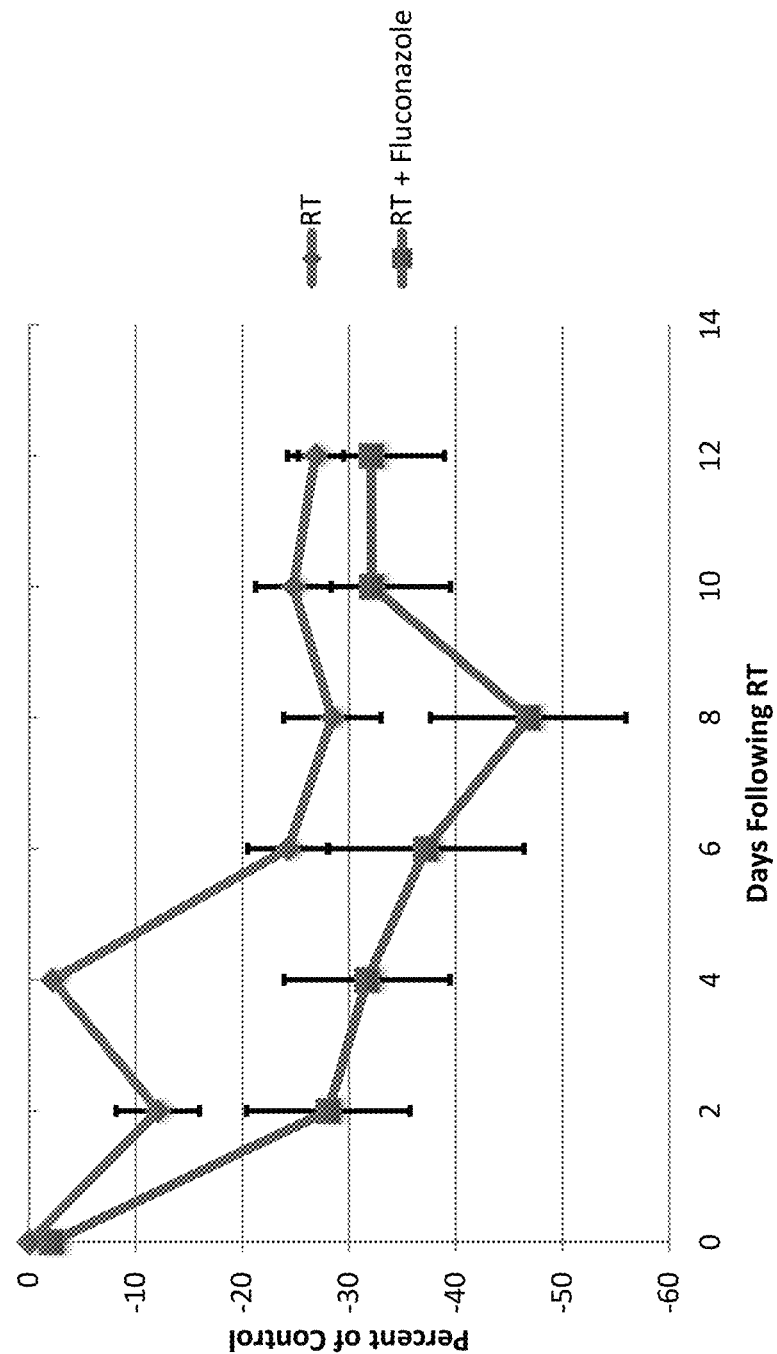
FIGS. 12A-12B depict that treatment with antifungals increases the efficacy of RT, in accordance with various embodiments of the invention.
Figure 12B:
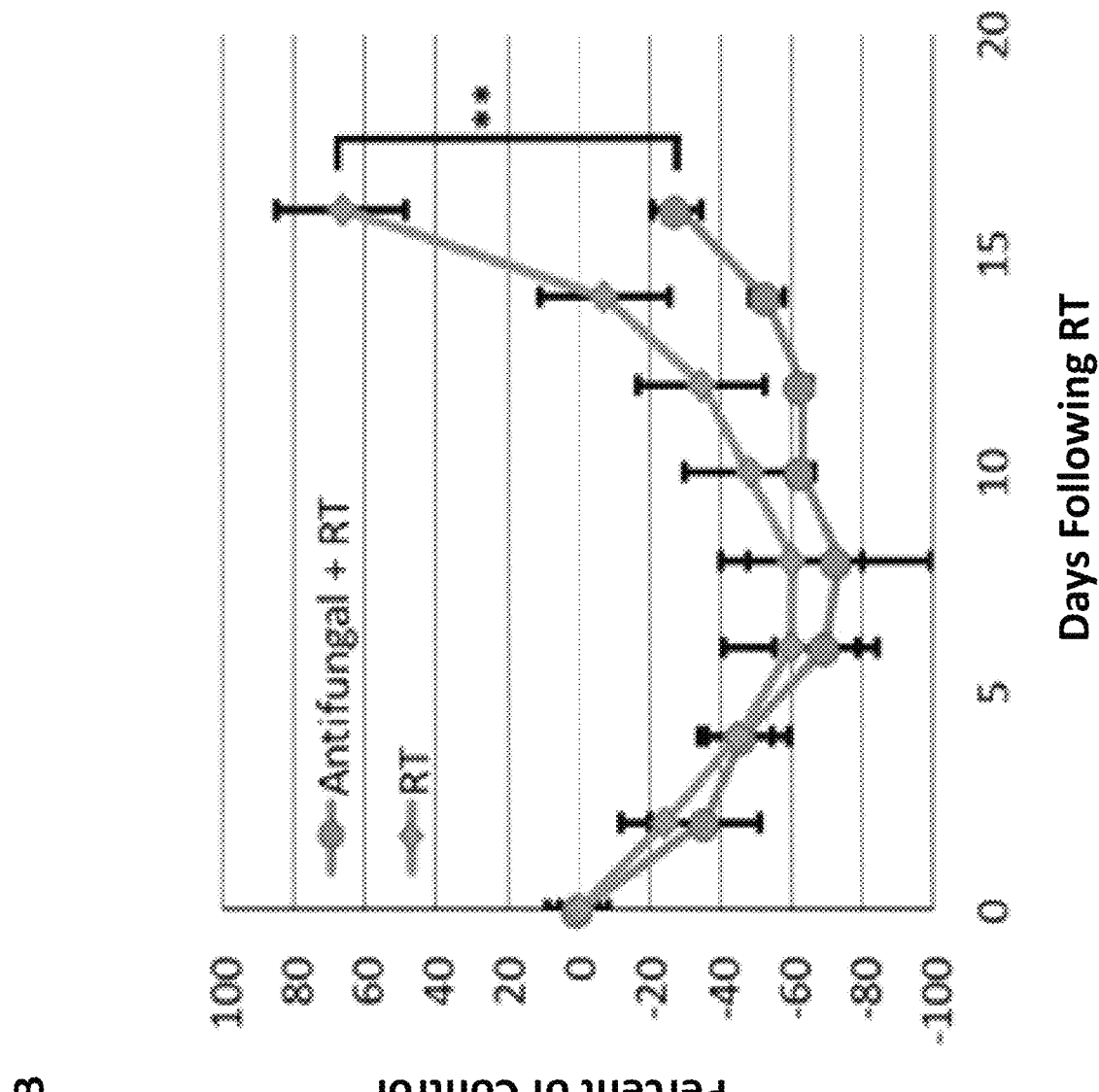

Bacterial- and Fungal-Targeted Dysbiosis Have Opposing Effects on the Efficacy of RT Orthotopic syngeneic PyMT transplantation in mice treated with a combination of antibiotics (Abx) administered in the drinking water were used to assess if bacterial microbiota would reduce the response to RT. It was observed in several experiments using multiple different broad-spectrum antibiotics that depletion of bacterial microbiota reduced the efficacy of RT of breast cancer (12 Gray (Gy), single-fraction; FIG. 8B). In contrast, a series of experiments where the fungal microbiota was disrupted with a cocktail of antifungal agents (AF; fluconazole, 5-flurocytosine and amphotericin B) showed a significantly enhanced response to RT with a prolonged delay in tumor regrowth following treatment (FIG. 12B). Without being bound to any particular theory, these data indicate that reprogramming immune microenvironments by targeting/modulating the bacterial and fungal microbiomes may alter the survival of breast cancer patients by enhancing sensitivity to cytotoxic therapy.

Effect of Bacterial and Fungal Depletion on Different Doses of RT

In studies so far, a single, experimentally determined dose of RT (12 Gy, single-fraction) that we observed would delay tumor growth when delivered alone was used. Studies in experimental and clinical settings have shown that the dose and number of fractions delivered to a tumor can impact the anti-tumor immune response elicited by RT. Clinically, RT is typically delivered over multiple daily fractions (fractionated RT) ranging from 1 to 7 weeks, though advances in RT delivery have allowed for increasingly larger doses to be delivered safely, and clinical trials with these larger doses have demonstrated improved local efficacy. Studies in a humanized mouse model of melanoma suggest that low dose RT (2 Gy) can prime the immune system, whereas other studies have shown in mouse models of breast cancer that multiple, larger doses (8-20 Gy) produce the strongest anti-tumor immune response. Given the overall paucity of data regarding the most immunostimulatory dose of RT, the effect of targeted disruption of the bacterial and fungal microbiota in conjunction with several different doses and fraction numbers was explored, to characterize the role the microbiome plays in shaping the RT-induced anti-tumor immune responses.

To better model the doses and type of RT that is delivered clinically, an X-RAD Small Animal Image Guided Irradiation System (SmART) developed by Precision X-Ray was installed. This device combines 3D volumetric imaging (computerized tomography) and optical imaging with accurate specimen positioning, allowing for precise, conformal image-guided radiation therapy to specific targets in mice. This approach allows for delivering highly focused and well-quantified doses of radiation to tumors in mice in a manner that is essentially identical to that used in the clinic for breast cancer patients. It is far superior to using a cesium-source irradiator as is commonly employed in mouse studies.

Without being bound to any particular theory, we believe that the effect of RT-mediated anti-tumor immune responses on tumor growth depends on the presence of specific bacteria or fungi. Mammary tumorigenesis is evaluated in two settings: (1) where specific bacterial species are depleted using antibiotics that target that class of bacteria (e.g. vancomycin for gram positive, neomycin for gram negative or metronidazole for anaerobes) or (2) in the setting where specific fungal populations are depleted using antifungal agents (e.g. fluconazole).

Since the study endpoint is determined by tumor size, tumor growth is quantitatively measured every 3-days throughout the study using calipers. Tumors are harvested and evaluated at three endpoints: 1, 2, 4 and 10 days following RT. The leukocyte profile from treated and untreated tumors is evaluated by FACS and immunohistopathology as previously published (DeNardo, D. G., et al. Cancer discovery 1, 54-67 (2011). Cell surface markers, T cells, macrophages and DC subsets are evaluated for 1. activation and maturation status by flow cytometry, 2. cytokine profile by intracellular FACS or quantitative PCR (qPCR) on FACS-isolated cells, and 3. ex vivo activation analysis of cytokine production from sorted cells, as recently described (Shimada, K., et al. PLoS Pathog 5, e1000379 (2009). The typical yield from a 1.0-cm tumor when dissociated is approximately $2\text{-}3\times10^6$ cells—approximately $2.5\times 10^5$ cells are required for FACS; thus, sufficient immune cells can be analyzed in distinct populations, and 10 mice/group will provide sufficient statistical power using one way ANOVA followed by post hoc paired tests to reveal differences between treatment groups. Tumor histopathology is examined via immunohistochemical (IHC) and immunofluorescent (IF) approaches in paraffin-embedded and/or OCT-frozen tissue sections for other parameters regulating tumor progression including proliferation via BrdU, cell death via cleaved caspase-3, angiogenesis via CD31, and hypoxia via hypoxyprobe staining as previously published 35. (DeNardo, D. G., et al. Cancer Cell 16, 91-102 (2009) and Junankar, S., et al. J Invest Dermatology 126 Suppl, 36-43 (2006). Sections are analyzed by digital scanning and enumeration using the Aperio digital pathology system and quantitatively evaluated using the Student's T-test with significance at a p value <0.05 between groups. These data will reveal the activation and TH status of the individual leukocyte subtypes. In concert with leukocyte profiles, these parameters will reveal how experimental therapies influence the angiogenic, proliferative and apoptotic properties of the tumor and will shed light on potential mechanism(s) underlying the effect of therapy.

The relationship between the microbiome and the efficacy of RT are explored. Without being bound to any particular theory, we anticipate that in the absence of certain components of the microbiome, that the TH1 immune microenvironment induced following RT will have reduced anti-tumor bioactivity. Our studies reveal to what degree this response is mediated by varied presence or altered activation/maturation of TH1 CD4+ T cells, CD8+ T cells, T regulatory (Treg) cells, M1-type macrophages or other myeloid suppressive cells, accompanied by possibly more mature DCs (based on phenotypic markers such as MHC class II and cytokine expression, e.g. interferon (IFN)-γ, IL-12, Granzyme A and B). Alternatively, a distinct leukocyte subtype may not emerge as specifically important, but instead a shifted cytokine microenvironment may emerge (lower IFNγ, IL-17 and possibly elevated TGFβ) indicative of a "weaker" TH1-type anti-tumor state. Our experimental strategy will not discriminate but instead will monitor all possibilities. This detailed examination of RT-induced immune responses will identify potential molecular/cellular pathways to target therapeutically. Without being bound to any particular theory, one mechanism in which antibiotics may be affecting the response to RT is by increasing the ratio of CD4:CD8 T-cells.

Example 4

Immune Mechanism(s) of Bacterial and Fungal Microbiota Regulation of Tumor Responses to RT Without being bound to any particular theory, the inventors believe that depletion of bacteria will diminish TH1-mediated responses by reducing the anti-tumor activity of specific leukocyte subsets following RT, whereas depletion of fungi will enhance the TH1-mediated responses by eliminating the TH2 pro-tumor activity of specific leukocyte subsets. To address the molecular and/or cellular mechanisms underlying reduced chemo- and radiosensitivity following microbiome depletion, the orthotopic transplant model was utilized to reveal which leukocyte population or cytokines contribute to the diminished response following antibiotic or antifungal therapy using different genetically-deficient strains of mice lacking certain immune cells or blocking/depleting antibodies. The inventor's lab currently maintains or has ready access to syngeneic breeding colonies of mice genetically deficient for CD4+ T cells, CD8+ T cells, B cells, IL4Rα, IFN-γ and IL17, and has extensively published experience with cytokine/cell depleting monoclonal antibodies to eliminate CD4+ T cells, CD8+ T cells, Treg cells, macrophages, monocytes, DCs, as well as critical cytokines including IL4, IL10, IL12, IL17 and IFNγ. As above, mice are implanted in their mammary fat pads with syngeneic PyMT mammary tumor cells and primary tumors will be treated with RT with and without antibiotics or antifungal medications. The effect of microbiome depletion and RT was studied in mice deficient in the CD4+ T cells, CD8+ T cells, B cells, monocytes and DCs to elucidate which specific leukocyte populations may be important. More specific subsets and cytokines such as Treg cells, certain DC subsets, IL10, IL12, IL17 and IFNγ were tested depending on which leukocyte population was identified as being important for the effect. Mice that are genetically-deficient or specifically depleted of leukocyte subsets or cytokines will be compared and the effect on the growth parameters on the implanted tumors is assessed. Altered tumor growth kinetics are compared between immune-complete versus immune-modified groups following treatment with chemotherapy or RT and microbiome depletion. Tumor growth, immune profiles and parameters are quantitatively assessed using the Aperio digital pathology system and quantitatively evaluated using the one way ANOVA followed by post hoc paired tests with significance at a p value <0.05 between groups. Without being bound to any particular theory, we anticipate that the major cell type affected is CD8+ T cells. Thus, combined treatment mice in CD8-deficient recipients as well as CD8-depleted mice will be evaluated. These studies will reveal the degree to which diminished outcome by microbiome depletion and chemo/RT therapy is reliant upon CD8+ T cell responses. Moreover, since Treg cells as well as multiple myeloid cell types regulate anti-tumor activity of CD8+ T cells, we envision targeting these cellular mechanisms to determine if CD8+ anti-tumor responses can be manipulated by removing these cell types. Cytokine depletion would proceed as the data indicate to evaluate if instead the altered cytokine milieu created by microbiome depletion instead regulates anti-tumor responses by CD8 T cells. Regardless of the mechanism, our studies are designed to reveal dominant pathways for generation of anti-tumor responses following chemo/RT-based therapy that are regulated by the microbiome. These in turn can be further manipulated in vivo to further explore augmentation of any responses revealed herein.

Figure 23:
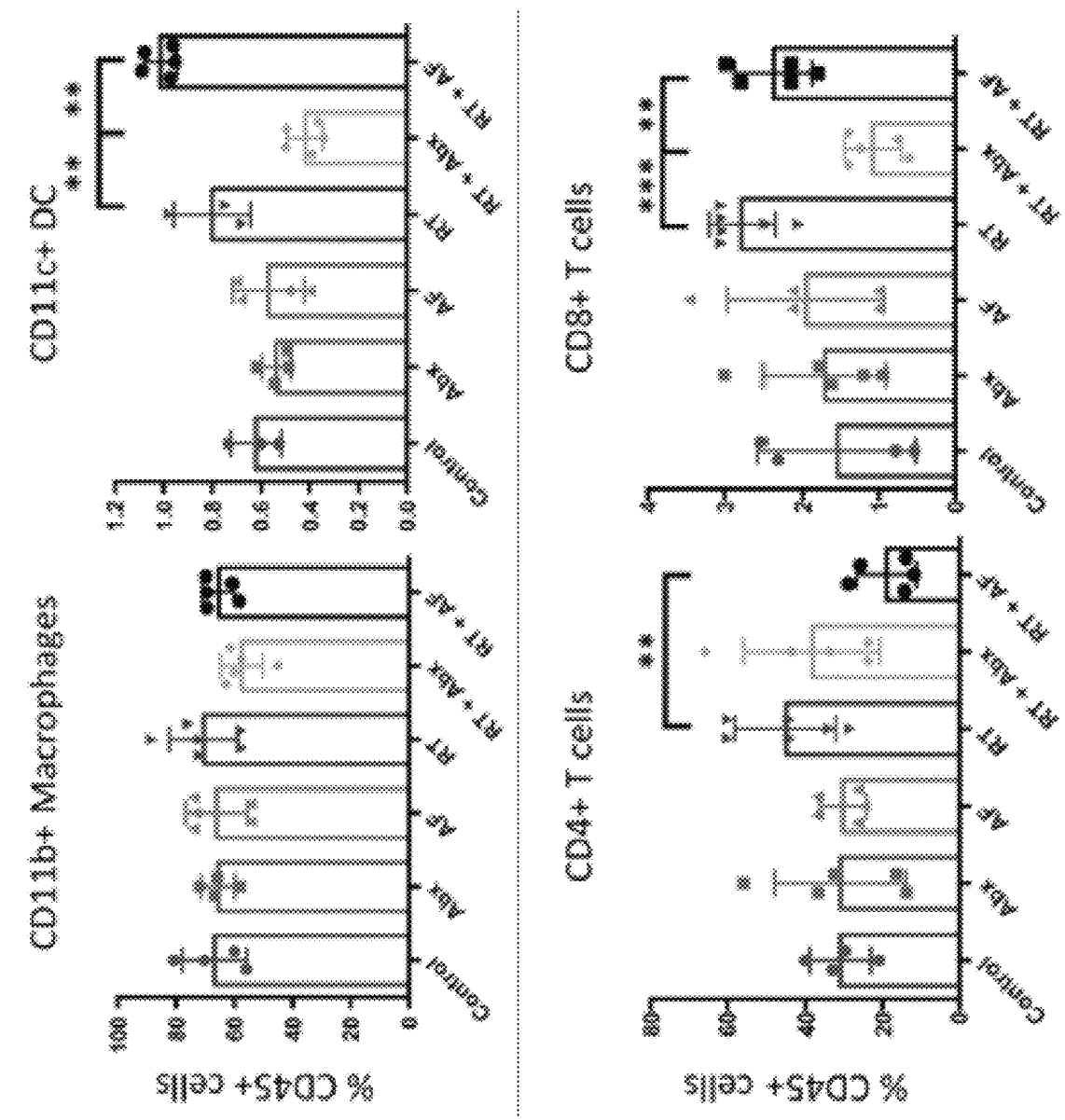
FIG. 23 depicts immune profiling and blockade experiments, in accordance with various embodiments of the invention. Tumors from mice that had been treated with RT and Abx/AF cocktails were analyzed by multicolor flow cytometry. Analysis of the cell populations were completed with the FlowJo software package (TreeStar). n=5/group, p<0.01, *p<0.001.

Studies have observed that the efficacy of RT and chemotherapy is mediated by CD4+ T cells and macrophages. The inventors studies revealed that CD4+ T cells, through a mechanism involving IL-4, alter the macrophage phenotype to limit the efficacy of RT and paclitaxel and that blockade of the IL-4 pathway significantly enhances the efficacy of both cytotoxic therapies. When tumors from mice that had received cocktails of antibiotic (Abx) or antifungals (AF) prior to RT were profiled, the inventors found that antibiotics significantly diminished the number of DCs and CD8+ T cells found within tumors consistent with their poor response to RT (FIG. 23). In contrast, antifungal treatment prior to RT significantly increased the number of intratumoral CD11c+ DC and reduced the number of CD4+ T cells (FIG. 23), which without being bound to any particular theory, suggests that the enhanced response to RT of tumors from mice treated with antifungals have a more favorable immune milieu with better antigen presentation and less immune suppression.

Example 5

Effect of Bacterial and Fungal Depletion on RT-Induced Systemic Anti-Tumor Immunity In addition to a local inflammatory response, several studies have demonstrated that RT can produce a systemic anti-tumor immune response targeting tumors outside of the irradiated field (an "abscopal" response). This RT-mediated abscopal effect depends on DCs and generating a productive cytotoxic CD8+ T cells. Recent studies from our lab have revealed that this systemic anti-tumor immune response can be highly potentiated by immunotherapy with immune checkpoint inhibitors, different immune agonists and combinations of the these two agents. In addition, several studies indicate that the bacterial microbiome regulates the tumor response to immunotherapy agents. Studies in several mouse models have revealed that depletion of bacteria with antibiotics or the presence of specific bacterial species affects the efficacy of the immune checkpoint inhibitors anti-CTLA4 and anti-PD1/PDL1 mAbs. However, the effects of the fungal microbiome on the effect of immunotherapeutic agents remains unknown, and the impact of either the bacterial or fungal microbiome on the RT-induced abscopal response has not yet been described.

The orthotopic transplant model was used to understand the effect of the bacterial and fungal microbiome on the development of systemic anti-tumor immunity following RT in the mouse model of breast cancer. However, for these experiments 10 week old mice are implanted in two opposing mammary fat pads with syngeneic PyMT mammary tumor cells. Following approximately 3-4 weeks, antibiotics and/or antifungals will be administered. Mice are separated into various groups (Control, Abx, RT alone, Abx+RT, Control+anti-PD-1, Abx/AF+anti-PD1, RT+antiPD-q or Abx/AF+RT+antiPD-1). One tumor is treated with either a single dose (12 Gy) or multiple doses (9 Gy×3) of RT with and without antibiotics or antifungal medications. Both doses of RT have been described to optimally prime a systemic immune response following RT in murine models. Fecal pellets are collected for approximately 2-3 weeks following treatment for bacterial 16S or fungal ITS2 sequencing analysis. After 2-3 weeks, tumor samples are obtained and FACS, cytokine and IHC analysis are performed. Tumor growth will be monitored for both tumors and altered tumor growth kinetics will be compared between bacterial and fungal depleted groups following treatment. As the abscopal effect mediated by RT alone is difficult to elicit, we also explore the role of the bacterial and fungal microbiome in the RT-induced abscopal response in the presence of the checkpoint inhibitor anti-PD1 or anti-CTLA-4. Tumor growth, immune profiles and parameters are quantitatively assessed using the Aperio digital pathology system and quantitatively evaluated using the Student's T-test with significance at a p value <0.05 between groups.

Without being bound to any particular theory, we believe that in the absence of certain components of the microbiome that the TH1 immune microenvironment induced following RT will have reduced anti-tumor bioactivity both in the primary tumor and for disease outside the irradiated field. These studies will reveal to what degree this response is mediated by the varied presence or altered activation/maturation of TH1 CD4+ T cells, CD8+ T cells, T regulatory (Treg) cells, M1-type macrophages or other myeloid suppressive cells, accompanied by possibly more mature DCs (based on phenotypic markers such as MHC class II and cytokine expression, e.g. interferon (IFN)-γ, IL-12, Granzyme A and B). Alternatively, a distinct leukocyte subtype may not emerge as specifically important, but instead a shifted cytokine microenvironment may emerge (lower IFN γ, IL-17 and possibly elevated TGFb) indicative of a "weaker" TH1-type anti-tumor state.

Innate Immune Responses

The effect of microbiota depletion and RT in mice deficient in monocytes or DCs will be assessed to elucidate which specific innate leukocyte populations may be important. As above, mice will be implanted in their mammary fat pads with syngeneic PyMT mammary tumor cells, and primary tumors will or will not be treated with either single-dose or fractionated RT with and without antibiotics or antifungal medications. An anti-CSF1R antibody (AFS98) will be used to deplete macrophages or the CD11c-DTR transgenic mice in which a transgene for diphtheria toxin is under control of the CD11c promoter combined with diphtheria toxin administration will be used to deplete DCs which are CD11c+. Additionally, the affected immune cells/cytokines will also be evaluated for significance by comparing between mice that are genetically-deficient or specifically depleted of leukocyte subsets or cytokines as appropriate and following their effect on the growth parameters on the implanted tumors. Altered tumor growth kinetics will be compared between immune-complete versus immune-modified groups following treatment with chemotherapy or RT and microbiota depletion. Tumor growth will be followed with calipers; intratumoral immune profiles will be assessed via flow cytometry; and changes in angiogenesis, proliferation and apoptosis using the Aperio digital pathology system will be quantified. Resulting data will be evaluated using the Student's t-test with significance at a p value <0.05 between groups.

Adaptive Immune Responses

As above, mice will be implanted in their mammary fat pads with syngeneic PyMT mammary tumor cells and primary tumors will or will not be treated with either paclitaxel or RT with and without antibiotics or antifungal medications. The effect of microbiota depletion and RT in mice deficient in CD4+ T cells and CD8+ T cells will be assessed. Mice that have the key cytokines driving Th1 and Th2 polarization, IL-4 and IFN γ, will also be tested using blocking antibodies. This set of experiments will elucidate which specific leukocyte populations and polarizing cytokines mediate the effects seen on the efficacy of RT in the setting of bacterial and fungal dysbiosis. Additionally, immune cells/cytokines will also be evaluated for significance by comparing between mice that are genetically-deficient or specifically depleted of leukocyte subsets or cytokines as appropriate and following their effect on the growth parameters on the implanted tumors. Altered tumor growth kinetics will be compared between immune-complete versus immune modified groups following treatment with chemotherapy or RT and microbiome depletion. Tumor growth, immune profiles and parameters will be quantitatively assessed using the Aperio digital pathology system and quantitatively evaluated using the Student's T-test with significance at a p value <0.05 between groups.

Without being bound to any particular theory, these studies will reveal the degree to which diminished outcome by microbiota depletion and RT is reliant upon CD8+ T cell responses. Moreover, since multiple myeloid cell types regulate the anti-tumor activity of CD8+ T cells, it can be determine if targeting these cellular mechanisms via macrophage or dendritic cell depletion in the setting of antibiotic- and antifungal-driven dysbiosis can affect the response to RT. Cytokine depletion of IL-4 and IFN γ, would allow for the evaluation of weather an altered cytokine milieu created by microbiome depletion instead regulates antitumor responses by CD8+ T cells. Regardless of the mechanism, the studies are designed to reveal dominant pathways for generation of anti-tumor responses following radiation-based therapy that are regulated by the microbiome. These can, in turn, be further manipulated in vivo to further explore augmentation of any responses revealed herein. Recognizing that many immune-based mechanisms regulated by interactions with the microbiome may exist and may play an important role in the development of RT-mediated anti-tumor immunity, alternative immune subsets and cytokines such as Treg cells, myeloid-derived suppressor cells (MDSCs), IL10, IL12 and IL17 will also be studied.

Role of Specific Intestinal Fungi in Modulating the Efficacy of RT

Without being bound to any particular theory, the inventors believe that manipulation of specific fungal microbiota can enhance the RT induced anti-tumor immune response. As revealed by the inventor's preliminary data, fungal dysbiosis induced by anti-fungal treatment leads to enhanced anti-tumor immune responses following RT. Without being bound to any particular theory, the inventors believe that this is either due to increases in a specific fungal species that promotes anti-tumor immunity or the absence of a particular fungus that suppresses an antitumor immune response following RT. In either case, the effect could be either direct through interactions with the mucosal immune system, or indirect, such as through modulation of the bacterial microbiota. In order to test the role of the fungal microbiota in mediating the enhanced inflammatory response following RT, the effect of adding either specific pro-inflammatory or anti-inflammatory fungi to specially colonized germ-free mice that have a known stable bacteria microbiome (Altered Schaedler Flora, ASF), but lack fungi was evaluated. These stably colonized ASF mice are implanted with tumors, those tumors are treated with RT and their outgrowth followed and the resulting changes in immune infiltrates were analyzed.

Figure 9A:
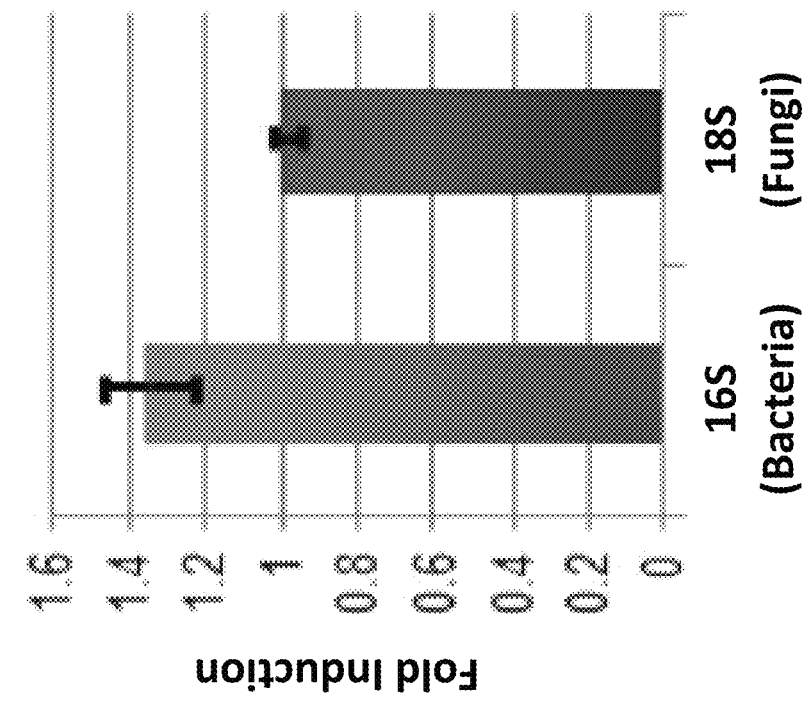
FIGS. 9A-9B depict bacterial and fungal quantitation, in accordance with various embodiments of the invention. The amount of bacteria (16S) and fungi (18S) in the feces were assessed by quantitative PCR one week following administration of either antibiotic vancomycin, imipenem and metronidazole (FIG. 9A) or antifungals fluconazole, 5-flurocytosine and amphotericin B (FIG. 9B). Antibiotics decrease bacterial 16S transcripts and increases fungal 18S transcripts, while antifungals show no effect on the quantity of bacterial or fungal populations.
Figure 9B:
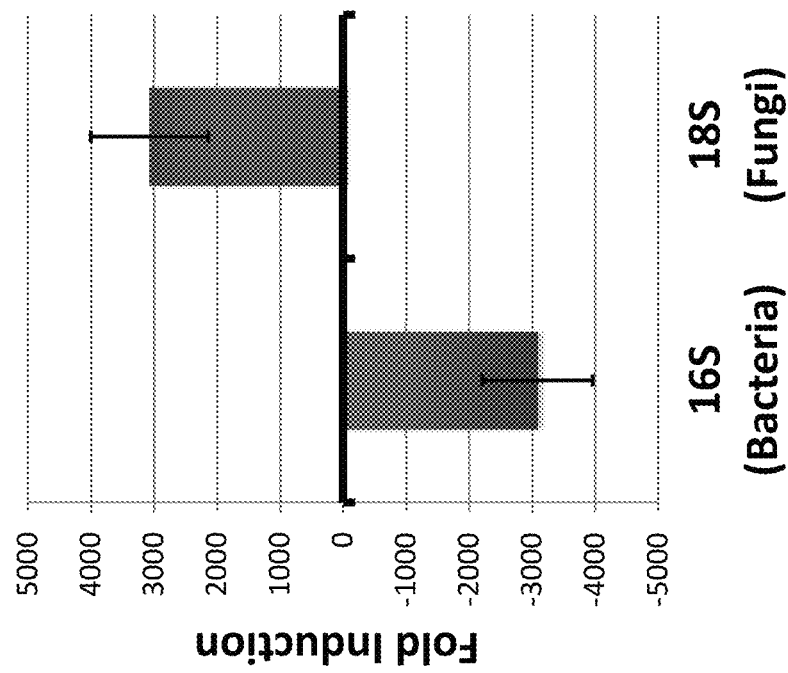
Figure 10:
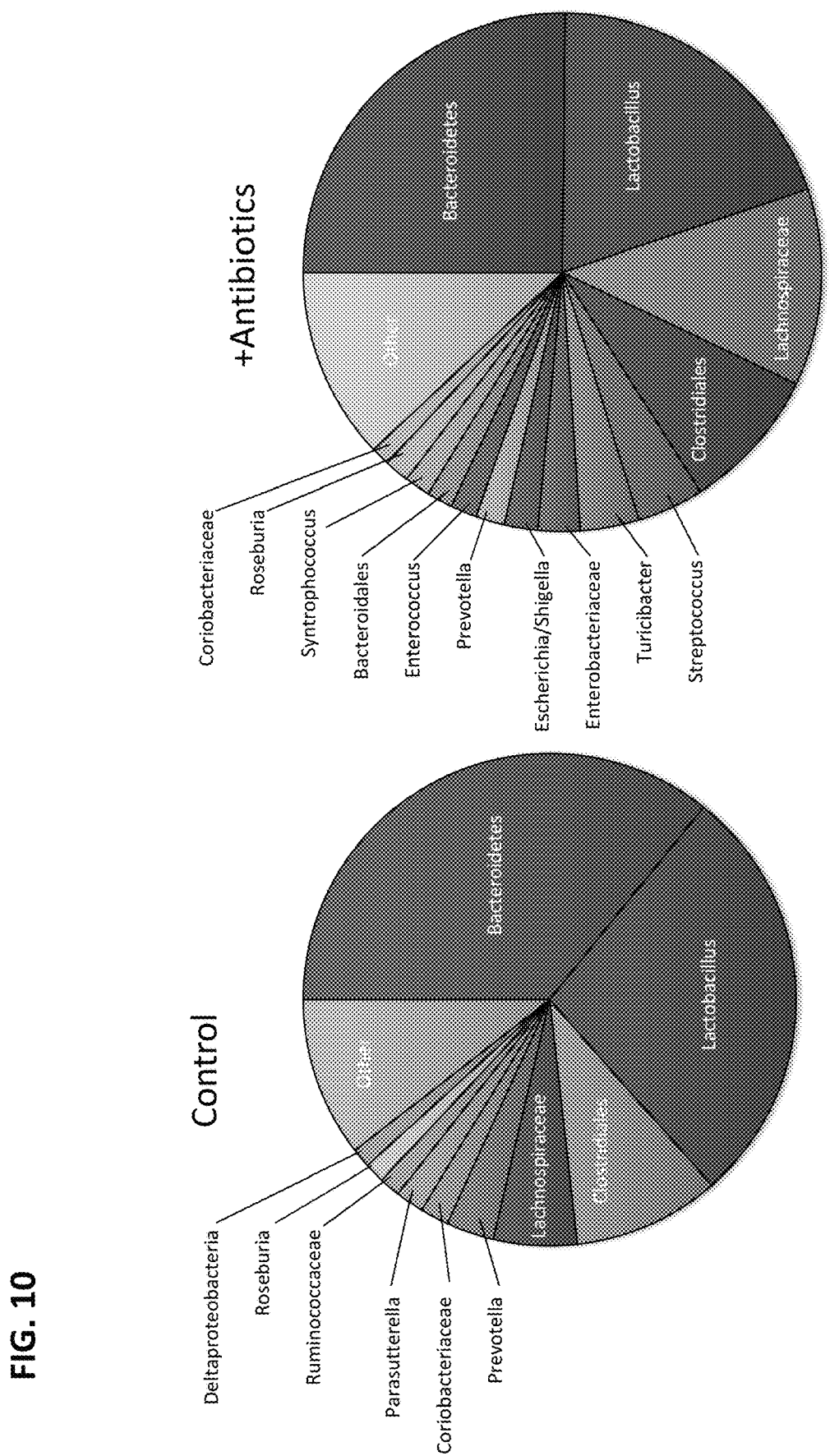
FIG. 10 depicts that antibiotics increase representation of rare species, in accordance with various embodiments of the invention.
Figure 11:
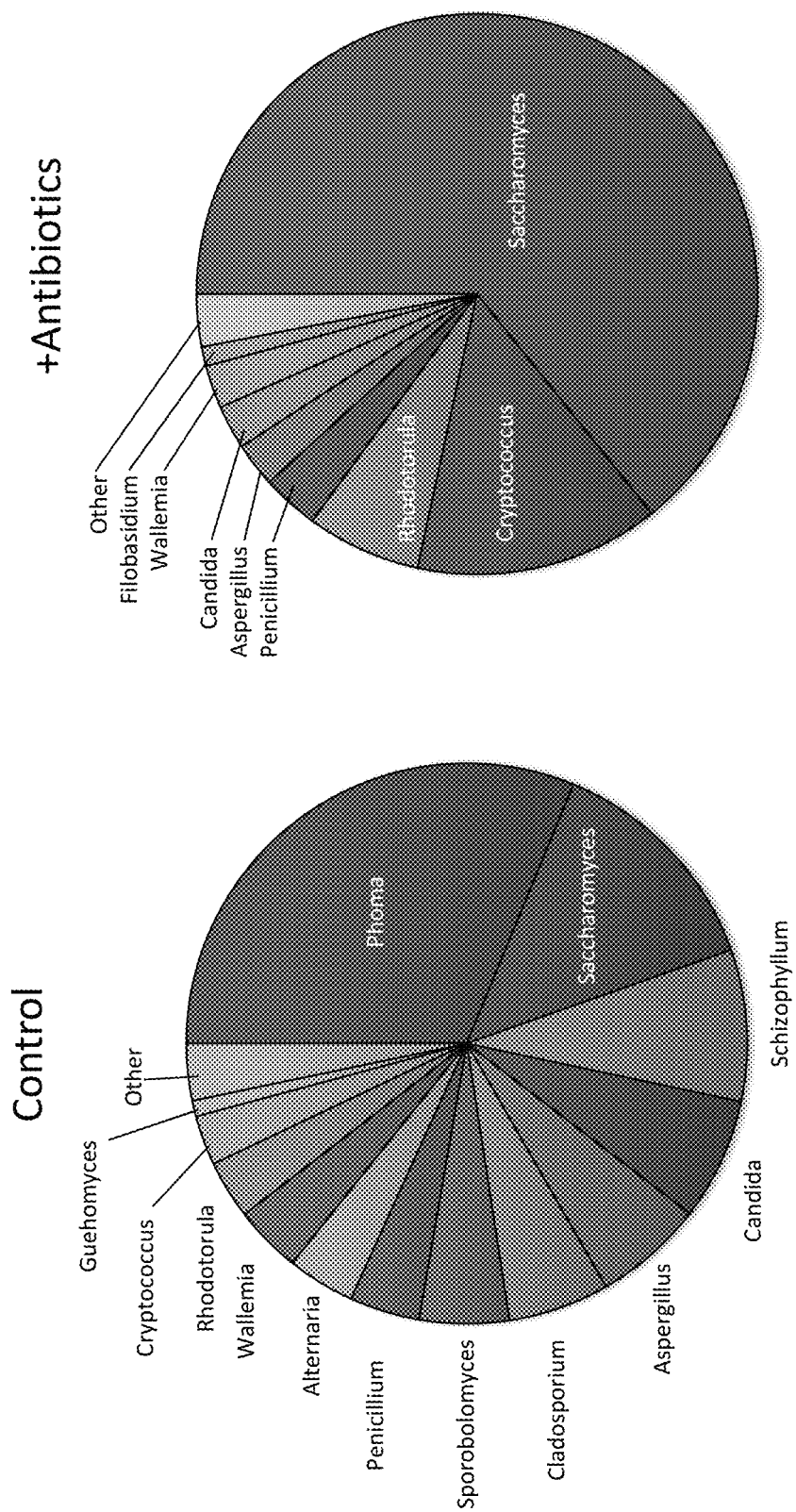
FIG. 11 depicts that antibiotics allow for overgrowth of only a few specific fungal species, in accordance with various embodiments of the invention.

Bacterial and fungal quantitation during antibiotic- and antifungal-induced dysbiosis was assessed using quantitative PCR to examine the relative quantity of bacteria and fungi in fecal pellets using 16S and 18S primers, respectively. The inventors found that antibiotic-induced dysbiosis leads to depletion of gut bacteria and a dramatic increase in the fungi found in the gut (FIG. 9A). The inventors estimate that the antibiotic cocktail used in these experiments produces >99% depletion of the bacterial population. Surprisingly, antifungal-induced dysbiosis had little effect on the quantity of either fungal or bacterial populations (FIG. 9B). Despite having little effect on the quantity of bacteria and fungi a dramatic difference is seen in the species represented in the antifungal treated group comparable to that seen with the antibiotic treated animals (discussed below).

In order to classify the bacterial and fungal species present in fecal samples, bioinformatic methods were used for the identification of bacterial/fungal species. The general approach was to PCR amplify rDNA segments, use high throughput sequencing approaches to read the variations in these sequences, and use bioinformatics approaches to assign a taxonomic designation to each sequence. Thus the presence and rough relative abundance of every species was determined. Taxonomic and/or species assignment of bacteria based on 16s ribosomal RNA gene sequencing has been widely applied in recent studies. These approaches typically group sequence reads by similarity into Operational Taxonomic Units (OTU). Each OTU is then compared to a reference database using BLAST or similar sequence alignment algorithms to determine the species with the closest matching known sequence. This OTU-based analysis has many practical benefits; one of the biggest advantages is the reduction in required computational resources or analysis time.

Unfortunately, applying similar methods to the identification of fungal species is problematic. First, the 18S rDNA gene is generally too conserved between fungi to be usable the way that the bacterial 16S gene is used. The solution to this problem has generally been to amplify one of the "internal transcribed spacer (ITS) regions" which encode the segments of RNA between the 18S and 5.6S or 5.6 and 28S rRNAs that are not used in ribosome biogenesis and are thus highly divergent. The inventors have employed a pipeline targeting the ITS1 region, by using a hand-curated and referenced database (ITF, current version 1.5) that is used systematically to accurately identify fungal DNA in human and mouse intestinal samples, which was developed by their collaborator, Dr. David Underhill. The inventors have observed that the majority of the sequences analyzed, aligned to at least one sequence in the database with a complete mapping percentage ≥97%.

Figure 24A:
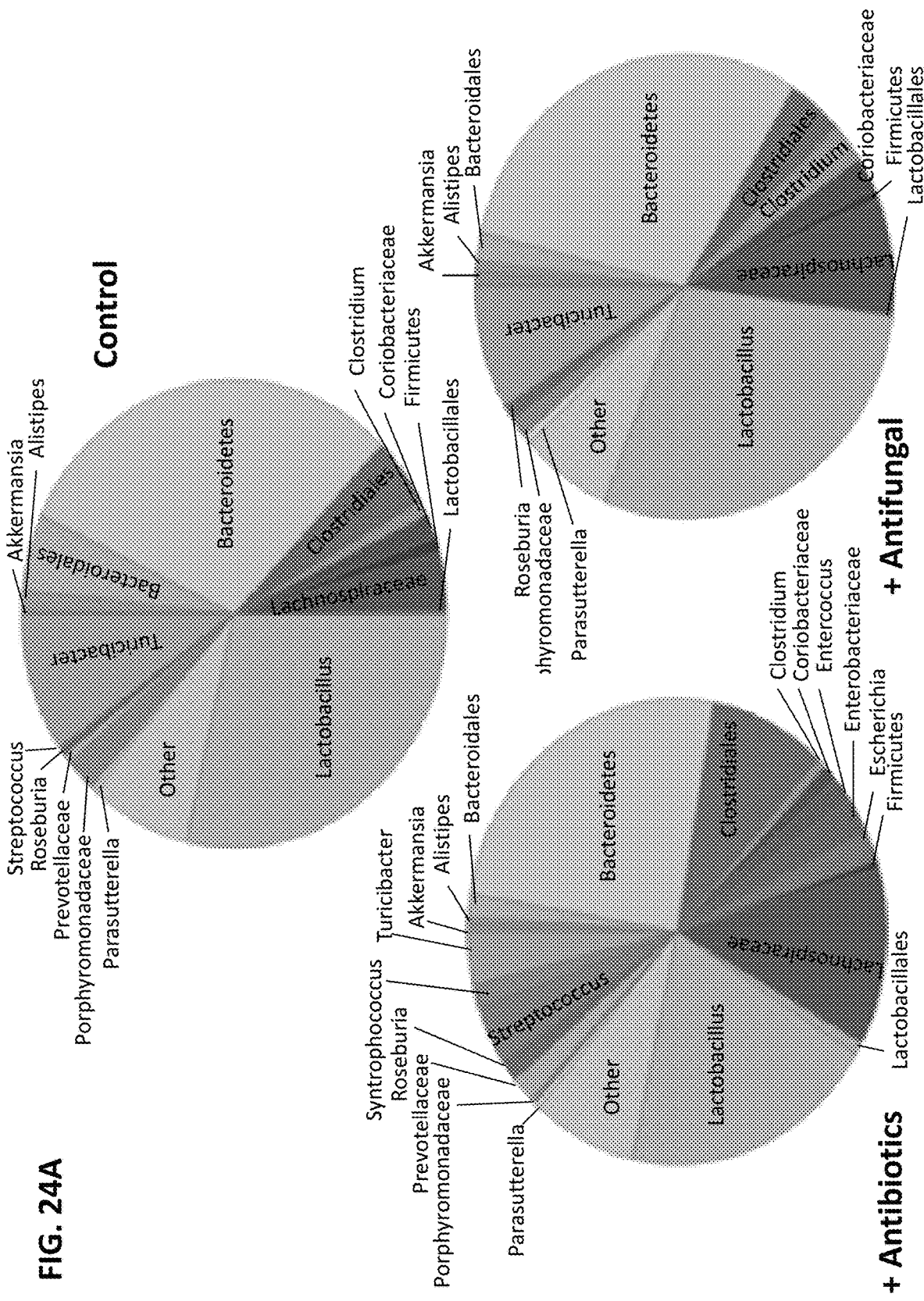
FIGS. 24A-24B depicts bacterial and fungal sequencing, in accordance with various embodiments of the invention.
Figure 24B:
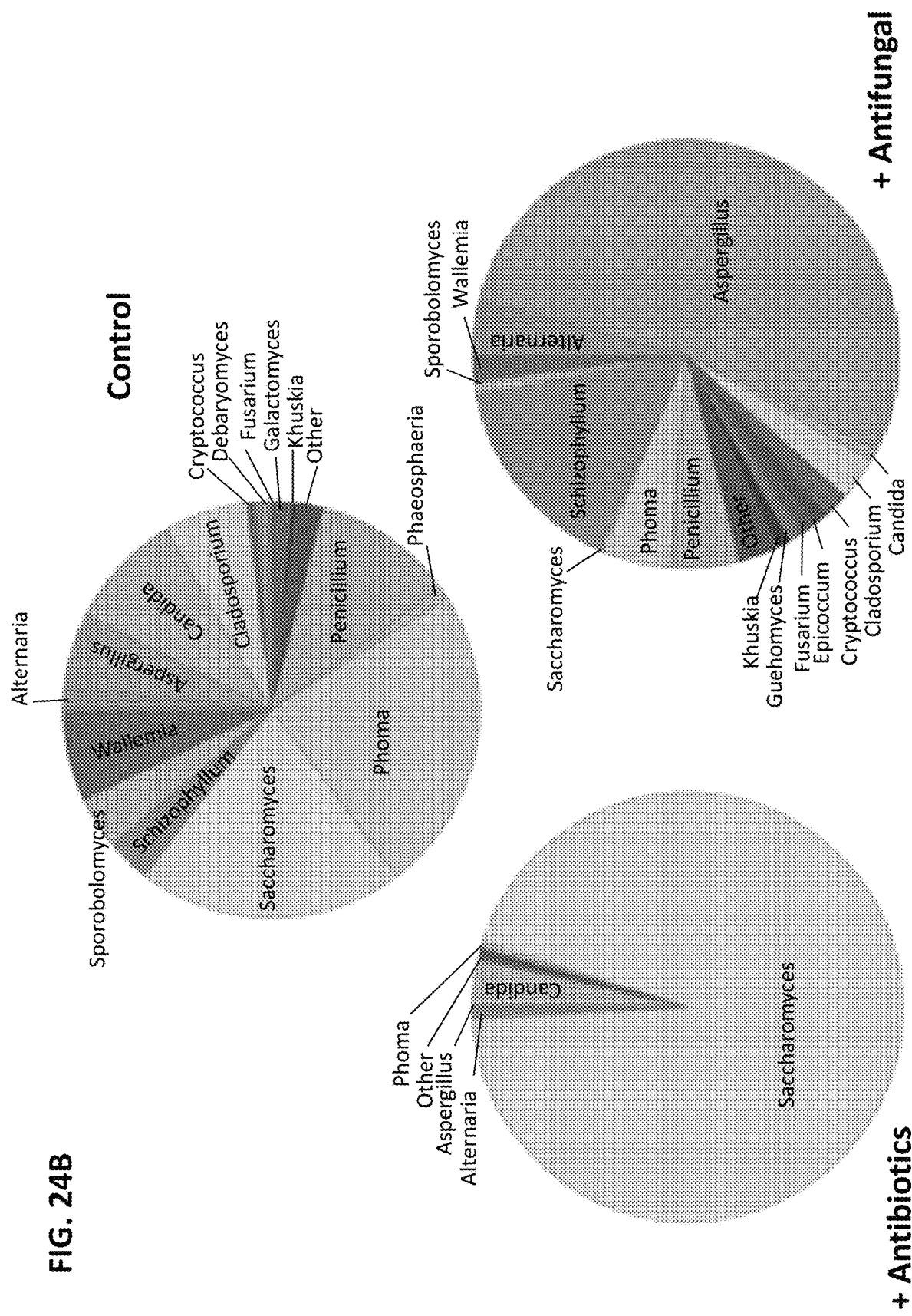

Using this pipeline, the inventors sequenced the feces from mice that had been treated with a cocktail of antibiotics or antifungals. Looking at the intestinal fungal mycobiome in these treated mice revealed several interesting observations: First, *Saccharomyces* and *Candida* species are the most prevalent commensal fungal species in the mice. Second, treatment with antifungals compared to untreated mice show significant changes in the populations of fungi and bacteria, most notably a dramatic increase in the *Aspergillus amstelodami* and a significant decrease in *Candida tropicalis* (FIGS. 24A and 24B). Without being bound to any particular theory, the inventors believe the enhanced efficacy of RT in antifungal treated mice results from either a rise in *Aspergillus amstelodami* or a reduction in *Candida tropicalis*. Interestingly, treatment with antibiotics caused tremendous overgrowth of *Saccharomyces cerevisiae* which, without being bound to any particular theory, the inventors further believe that the reduced efficacy of RT in antibiotic-treated mice could arise from the increase in *Saccharomyces cerevisiae* populations in the gut.

These studies take advantage of a unique opportunity to understand the etiology of the altered immune state following changes in the bacterial and fungal microflora. Previous studies by the inventors, demonstrate that gut fungal content regulates the inflammatory response in murine models of inducible colitis and asthma through a signaling pathway involving Dectin-11.

Figure 25:
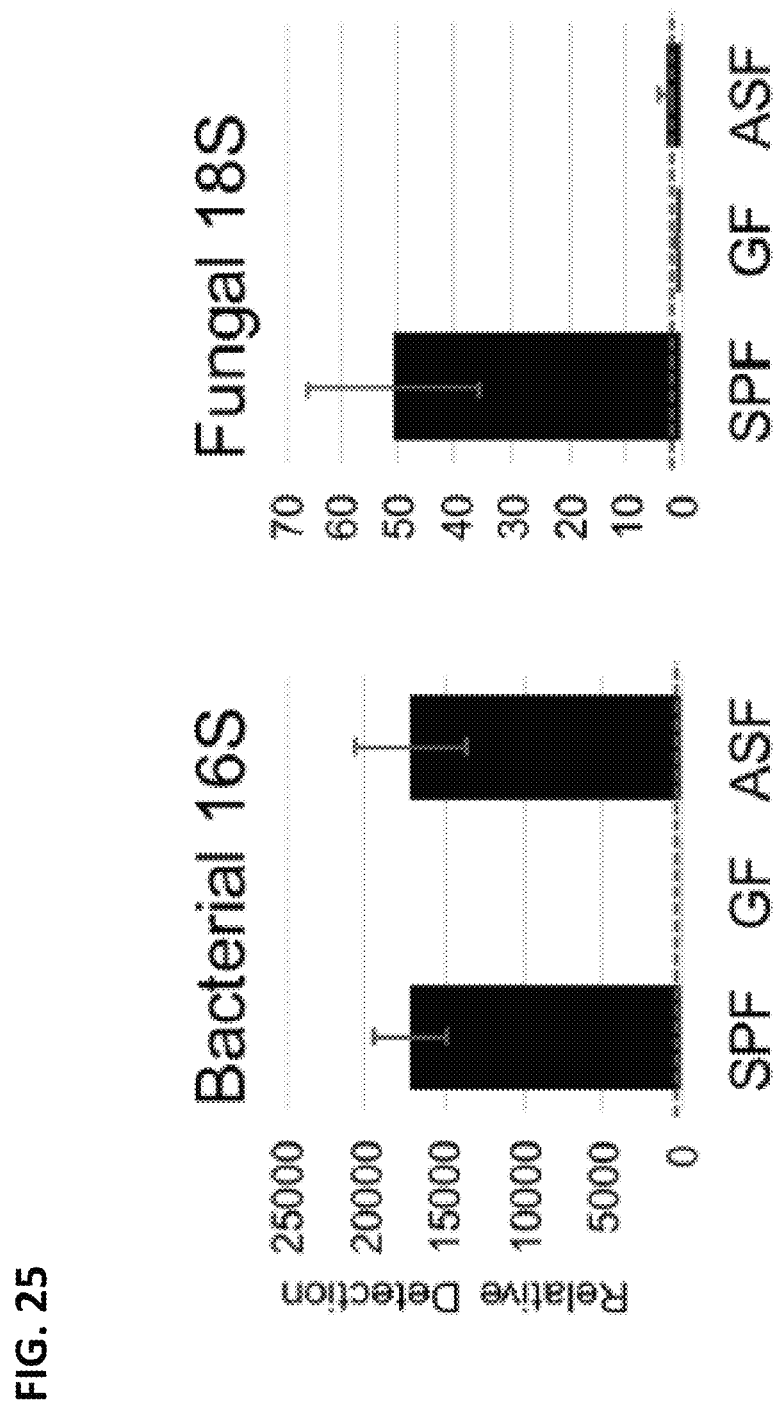
FIG. 25 depicts the generation of fungi-free animals, in accordance with various embodiments of the invention. Fecal pellets from specific pathogen-free (SPF), germ-free (GF), or altered Schaedler flora (ASF) mice were collected, DNA was isolated and bacterial 16S rDNA (left) and fungal 18S rDNA (right) were detected by quantitative PCR.

Like their human counterparts, rodents typically harbor trillions of bacteria and fungi, however germ-free (GF) animals are completely free of any microbiota. Initially created by aseptic cesarean section, once established a germ-free colony is maintained in sterile incubators for their whole lives. Germ-free status is verified by recurrent and frequent testing of their feces for any contamination. A common approach to investigating the role(s) of specific microbes in the host is to "monocolonize" GF mice with an individual organism. Interpreting results from these experiments can often be complicated by the fact that the immune system in GF mice remains immature given that intestinal microbiota are important for development of a mature immune system. A related approach, one that is ideally suited to the goals of these experiments, is to colonize mice with a minimal, defined pool of bacteria. One such bacterial population is a defined set of bacteria known as altered Schaedler flora (ASF). ASF consists of a community of eight bacterial species: two *Lactobacilli*, one *Bacteroides*, one spiral bacteria of the *Flexistipes* genus, and four extremely oxygen sensitive (EOS) *Fusobacterium species*. These bacteria were selected based on their dominance in the murine microflora and, compared to germfree animals, ASF mice have fully developed immune systems, resistance to opportunistic pathogens, and normal GI function and health, and are considered a good representation of normal mice. Fungi-free ASF mice were generated in the laboratory of David Underhill by gavaging germ-free mice with ASF inoculum and maintaining the resulting colony in sterile incubators (FIG. 25). Importantly, these otherwise healthy mice are not colonized with any fungi as verified by recurrent and frequent testing of their feces for any contamination.

Figure 27A:
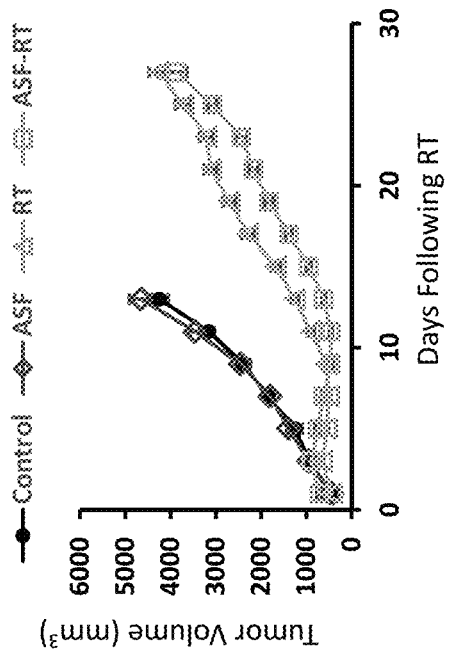
FIGS. 27A-27D depict Fungal-free mice and other antifungals similarly enhance the efficacy of RT, in accordance with various embodiments of the invention. Orthotopic E0771 mammary tumors were grown as described above and then treated with either the antifungal (5-fluorocytosine) one week prior to treatment with localized kV irradiation (16 Gy) (n=8 per group, one of two repeats shown) (FIG. 27A). Orthotopic tumors were then implanted in either normal mice or mice colonized with only altered Schaedler flora (ASF) which is a defined bacterial population that contains no fungi and subsequently irradiated. Tumor growth and survival were then assessed every three days (n=7 per group) (FIG. 27B, FIG. 27C). The amount of bacteria (16S) and fungi (18S) from mice treated with antibiotics were then assessed using qPCR (FIG. 27D).
Figure 27B:
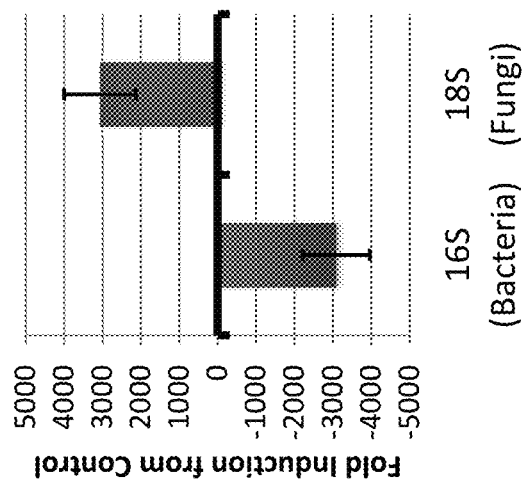
Figure 27C:
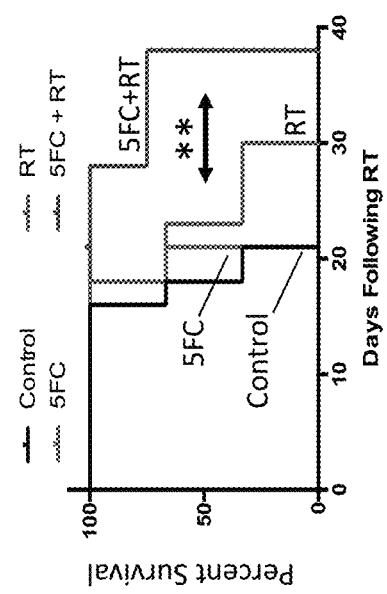
Figure 27D:
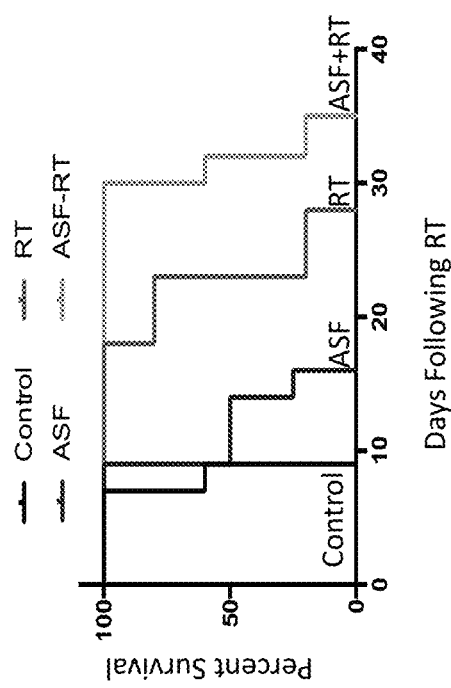
Figure 28B:
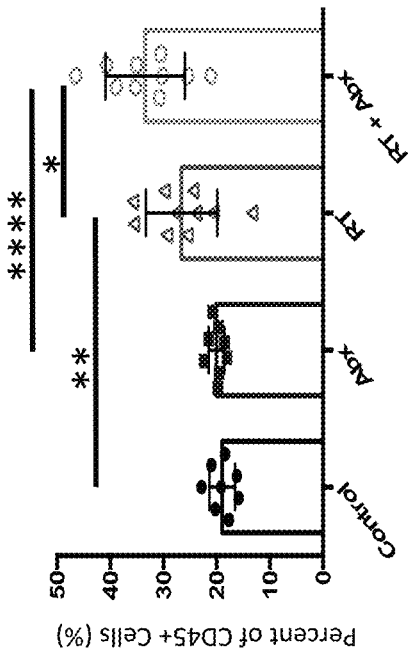
Figure 28A:
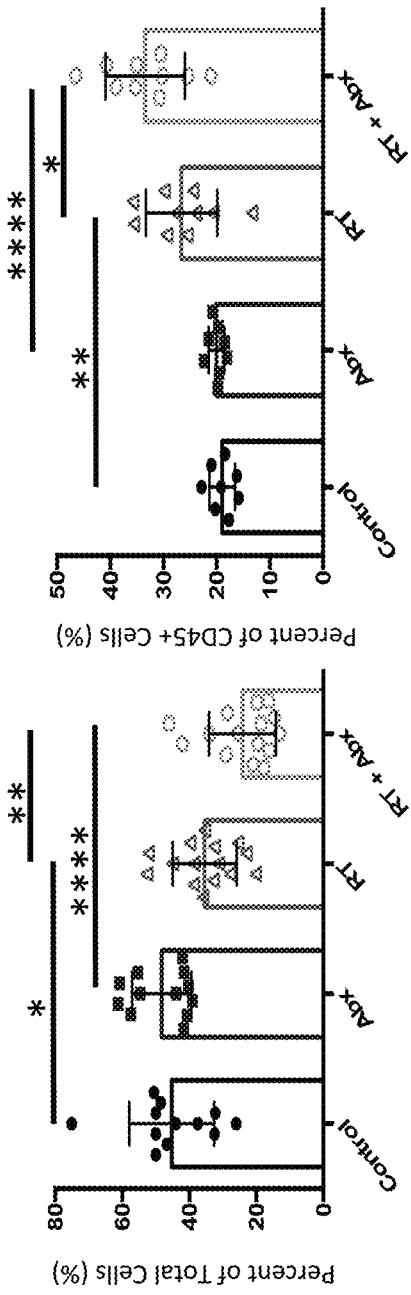
Figure 28D:
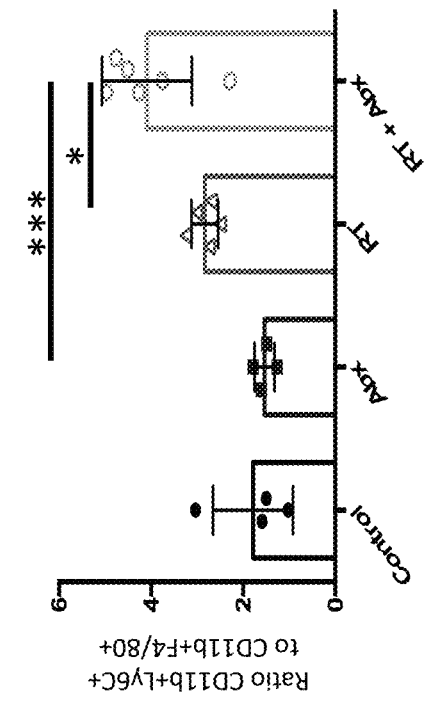
Figure 28C:
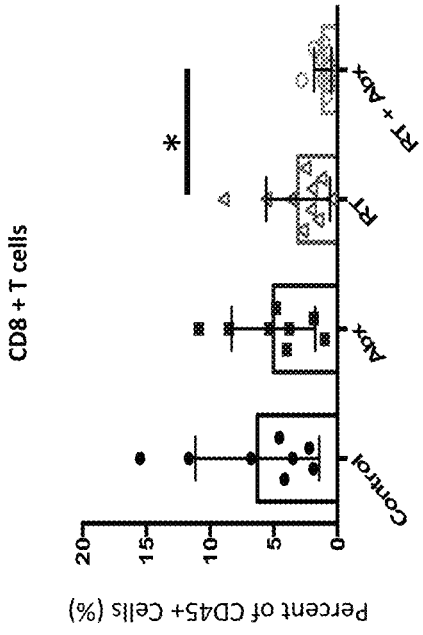

Orthotopic E0771 mammary tumors were grown as described above and then treated with either the antifungal (5-fluorocytosine) one week prior to treatment with localized kV irradiation (16 Gy) (n=8 per group, one of two repeats shown) (FIG. 27A). Orthotopic tumors were then implanted in either normal mice or mice colonized with only altered Schaedler flora (ASF) which is a defined bacterial population that contains no fungi and subsequently irradiated. Tumor growth and survival were then assessed every three days (n=7 per group) (FIG. 27B and FIG. 27C). The amount of bacteria (16S) and fungi (18S) from mice treated with antibiotics were then assessed using qPCR (FIG. 27D). These results demonstrate that fungal-free mice and other antifungals similarly enhance the efficacy of RT.

These ASF-colonized mice will be further colonized with a single fungal species in order to dissect the impact of the specific fungal species identified as potentially most significant in our initial experiments on the effects of antibiotic and antifungal treatments on the efficacy of RT-induced anti-tumor immunity.

Role of *Aspergillus Amstelodami* in Enhancing RT-Mediated Anti-Tumor Immunity

The effect of *Aspergillus amstelodami* on the RT-induced anti-tumor immune response was tested. ITS sequencing from our studies of antifungal treatment and enhanced RT efficacy revealed dramatic expansion of *Aspergillus amstelodami* when mice were treated with a cocktail of antifungal agents prior to RT (FIG. 24B). The inventors findings were consistent with their recently published data showing that *Aspergillus amstelodami* can exacerbate asthma in a mouse model of allergy. To understand whether this expansion mediated the significantly improved efficacy of RT, the inventors will implant tumors in ASF mice further colonized or not with *Aspergillus amstelodami*. These mice will have defined bacterial microbiota with a single fungal population allowing for the examination of the role of the individual fungal species. The effects (if any) of *Aspergillus* colonization on the ASF bacterial species will be characterized by 16S sequencing. For comparison, the inventors will implant tumors in normal specific pathogen free (SPF) mice exposed or not to *A. amstelodami* by oral gavage. Any effects of exposure to *Aspergillus* on the SPF bacterial microbiota will be characterized by 16S sequencing of fecal pellets. Tumors will be irradiated once they have reached approximately 1.0 cm. RT will consist of a single dose of 12 Gy to the tumor using our small animal irradiator XRAD SmART as outlined above, and we will evaluate anti-tumor efficacy.

Figure 5:
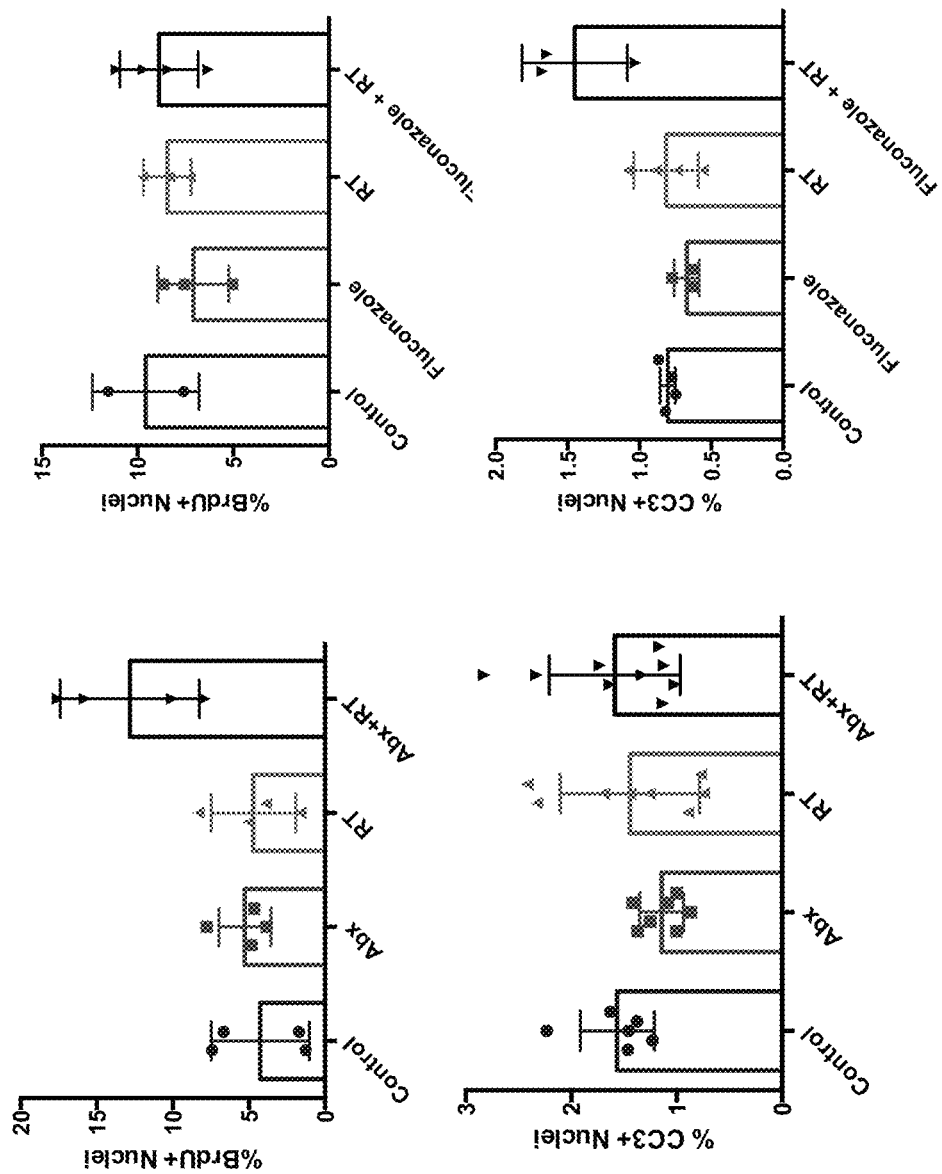
FIG. 5 depicts that tumors from antibiotic-treated mice divide more and undergo less apoptosis. The opposite is true for fluconazole treated mice. Abx: Vancomycin, Imipenem/Cilastin and Streptomycin.
Figure 6:
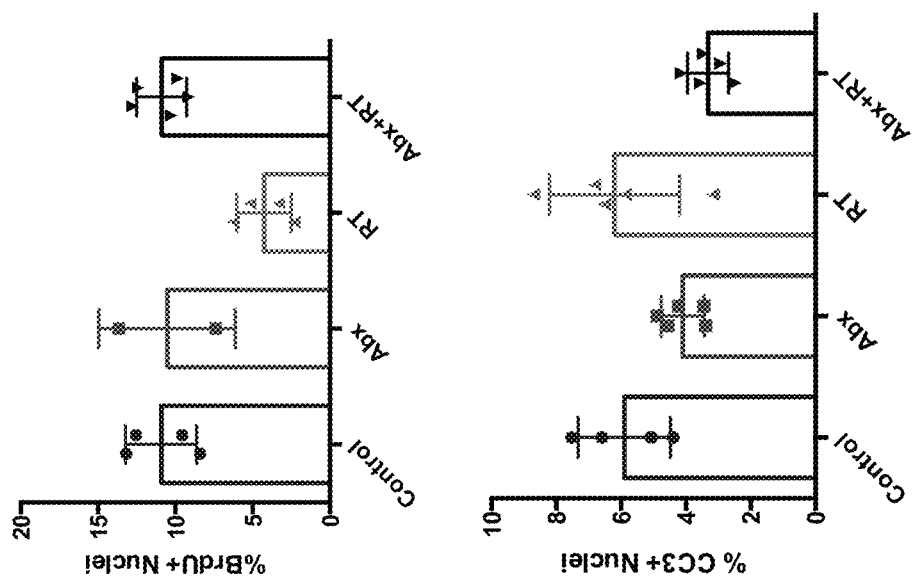
FIG. 6 depicts an increase in cell division and decrease in cell death with antibiotics and radiation, which is even more pronounced at short time points. Abx: Vancomycin, Imipenem/Cilastin and Streptomycin.
Figure 7:
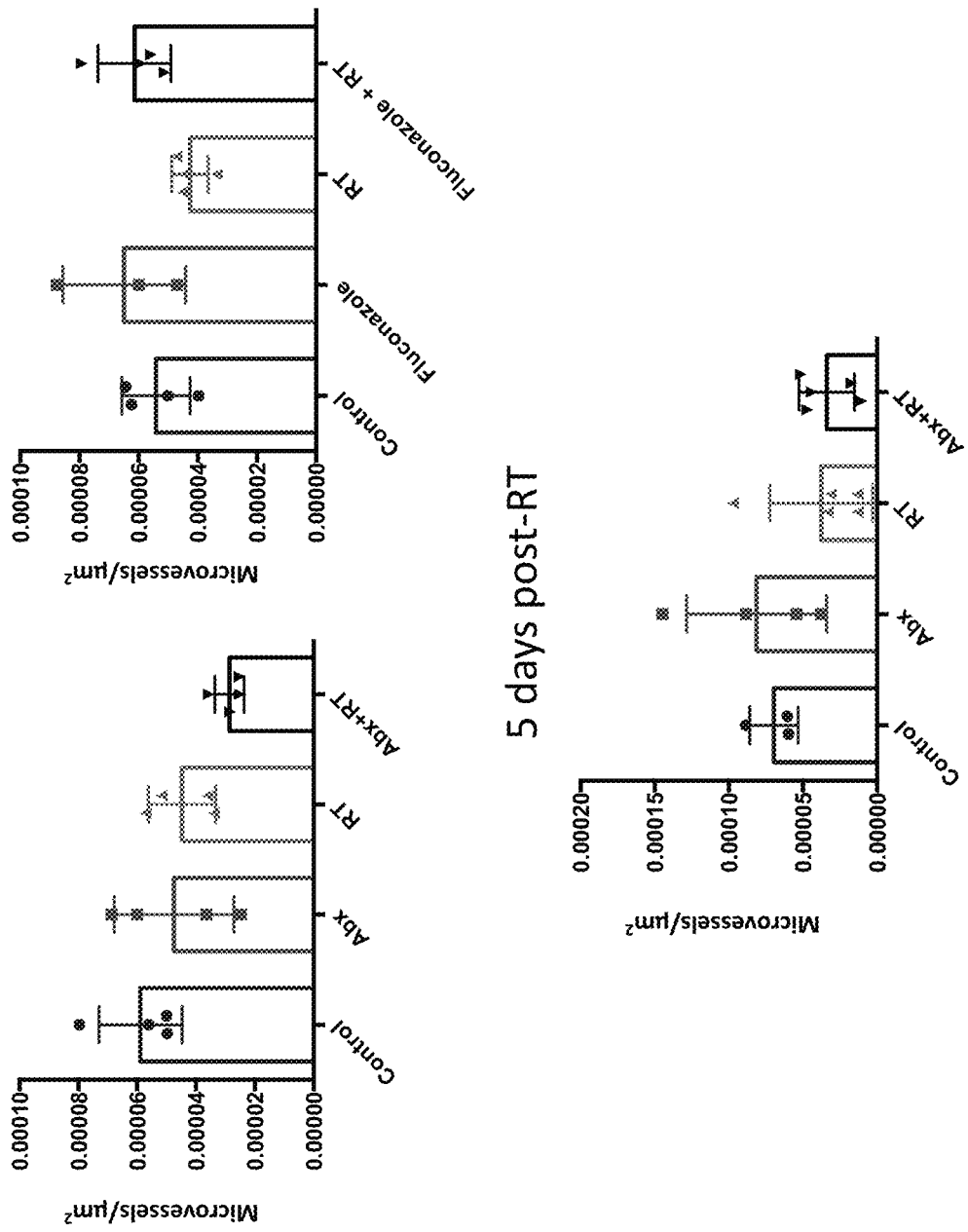
FIG. 7 depicts tumors from antibiotic-treated mice with fewer vessels after radiation. Abx: Vancomycin, Imipenem/Cilastin and Streptomycin.
Figure 22A:
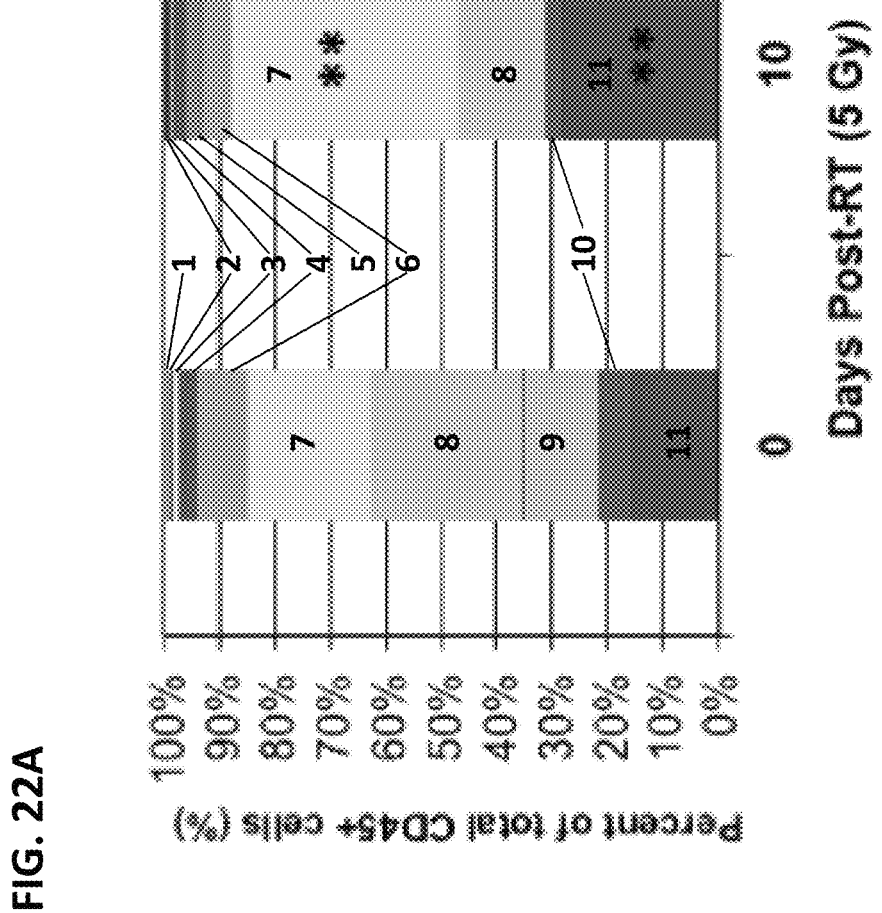
FIGS. 22A-22C depict the characterization of tumors in irradiated mice, in accordance with various embodiments of the invention. Tumors were harvested from mice at various time points and analyzed by flow cytometry (FACS) (FIG. 22A), immunohistochemistry (IHC) (FIG. 22B) and qPCR (FIG. 22C).
Figure 22B:
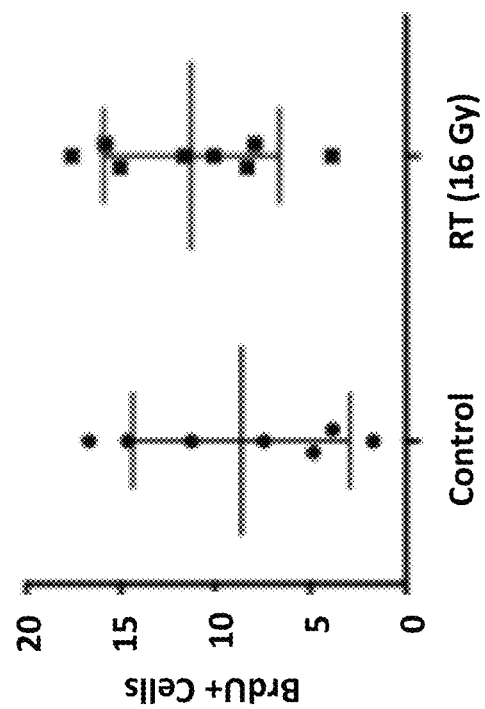
Figure 22B:
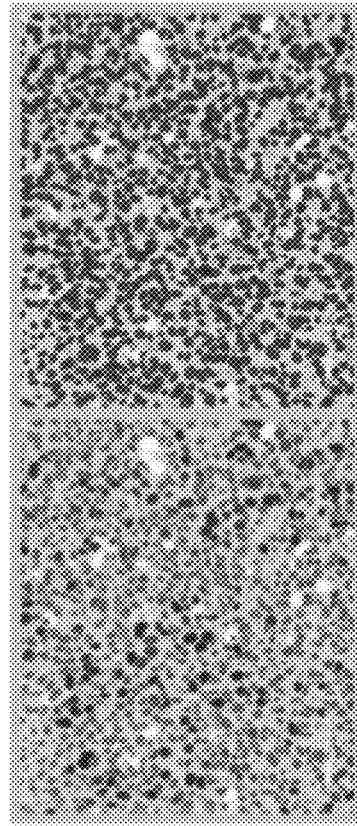
Figure 22C:
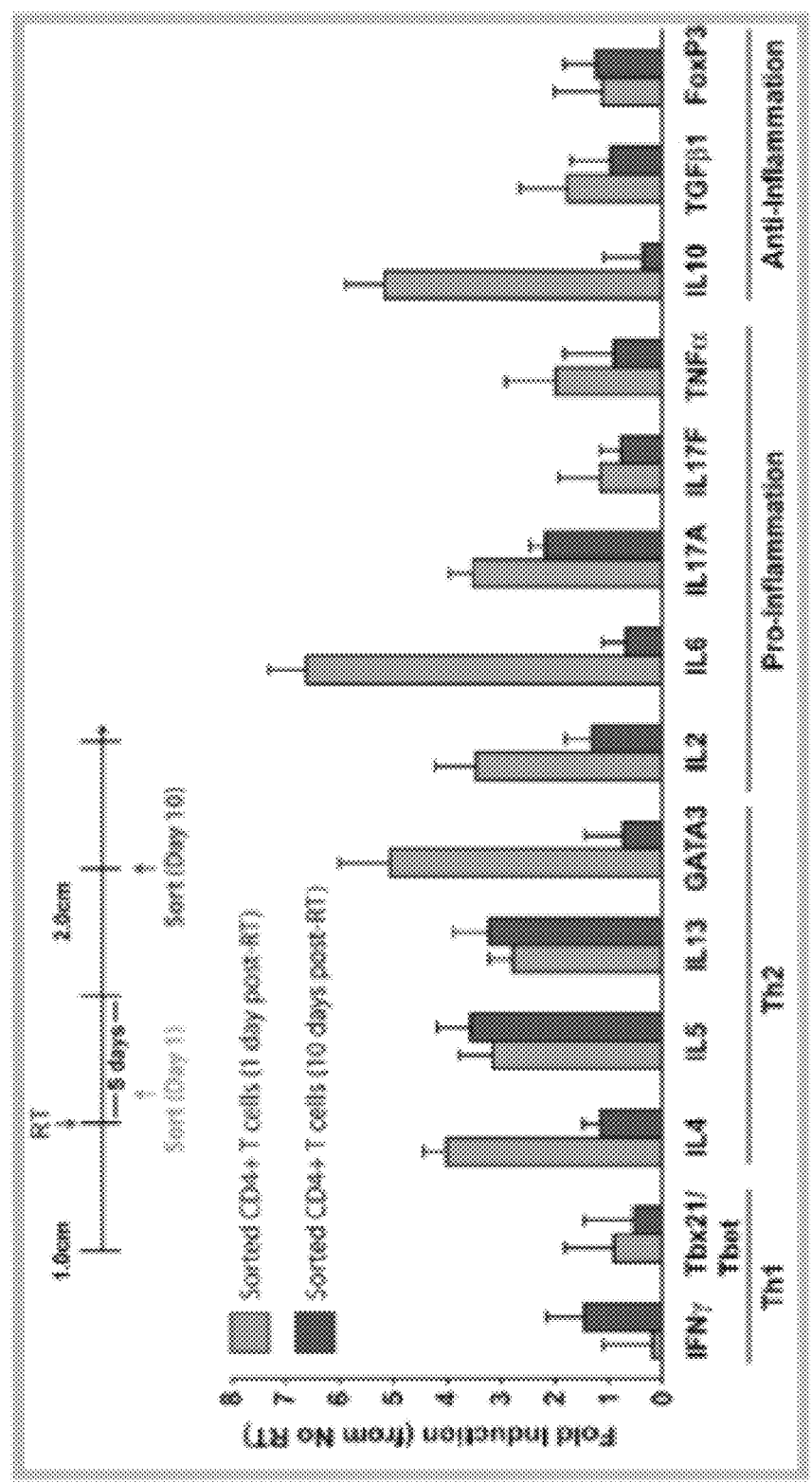

Tumor growth will be quantitatively measured every 3-days throughout the studies using calipers. Tumors will be evaluated at three endpoints: 1, 4 and 10 days following RT. The leukocyte profile from untreated and treated tumors will be evaluated by FACS and immunohistopathology similar to that shown in FIGS. 22A-C and FIG. 23. In addition to cell surface markers, T cell, macrophage and DC subsets will be evaluated for: 1) activation and maturation status, 2) cytokine profile by intracellular FACS or quantitative PCR (qPCR) on FACS-isolated cells, and 3) ex vivo activation analysis of cytokine production from sorted cells, similar to that described and shown in FIG. 22A-C. These data will reveal the activation and TH status of the individual leukocyte subtypes following colonization with a single fungal species. Tumor histopathology will be examined via immunohistochemical (IHC) and immunofluorescent (IF) approaches in paraffin-embedded and/or OCT-frozen tissue sections for other parameters regulating tumor progression including proliferation via BrdU, cell death via cleaved caspase-3, angiogenesis via CD31, and hypoxia via hypoxyprobe staining as shown in FIG. 5. Sections will be analyzed by digital scanning and enumeration using the Aperio digital pathology system and quantitatively evaluated using the Student's t-test with significance at a p value <0.05 between groups. Together these parameters, in concert with leukocyte profiles, will reveal how *Aspergillus amstelodami* influences the angiogenic, proliferative and apoptotic properties of a tumor and will shed light on potential mechanism(s) underlying the effect of this species on enhancing the efficacy of RT in breast cancer.

Role of *Candida Tropicalis* and *Saccharomyces Cerevisiae* in Suppressing RT-Mediated Antitumor Immunity The effect of two different fungal species, *Candida tropicalis* and *Saccharomyces cerevisiae*, will be tested in the mouse model of breast cancer. ITS sequencing from the inventors studies of antifungal treatment and enhanced RT efficacy revealed loss of *Candida tropicalis* species when mice were treated with a cocktail of antifungal agents prior to RT (FIG. 24B). Further, the inventors also discovered that treatment with an antibiotic cocktail led to significant expansion of *Saccharomyces cerevisiae* in the gut which correlated with reduced RT-mediated antitumor activity. These findings are consistent with experimental evidence showing that *Candida* can 1) regulate systemic immunity, 2) play a role in Crohn's disease, and 3) that its interactions with *Saccharomyces* shapes both innate and adaptive immunity. To understand whether the presence of *Candida tropicalis* or *Saccharomyces cerevisiae* can decrease the tumor response to RT, tumors will be implanted in ASF mice specifically further colonized with either *Candida tropicalis* or *Saccharomyces cerevisiae*. For comparison, tumors will also be implanted in normal specific pathogen free (SPF) mice exposed or not to *C. tropicalis* or *S. cervisiae* by oral gavage. Again, any effects of exposure to fungi on bacterial microbiota in both models will be characterized by 16S sequencing of fecal pellets. Tumors will be irradiated once they have reached approximately 1.0 cm. RT will consist of a single dose of 12 Gy to the tumor, and will be evaluated for anti-tumor efficacy as described above.

Without being bound to any particular theory, the inventors believe that either increased exposure to *A. amstelodami* will support increased RT efficacy and anti-tumor immune responses, or that increased *C. tropicalis* or *S. cervisiae* will lead to decreased RT efficacy and anti-tumor immune responses. Based on growing evidence that these fungi can influence the nature and magnitude of an immune response in diverse diseases including asthma and Crohn's disease, without being bound to any particular theory, there is reason to believe that they will also do so in the context of RT-mediated anti-tumor immunity. The effects of other bacteria and fungi or combinations thereof may also be explored based on the changes observed during antifungal and antibacterial treatments.

The data from these experiments will indicate how the anti-tumor immune response following RT is regulated by the intestinal microflora and provide the basis for human trials to explore the benefit of manipulating the microflora to shape the RT-mediated anti-tumor immune response.

Example 6

Methods

Stool from mice treated with the respective treatments (Antibiotics, Fluconazole, or nothing as a control) for one week, following RT, were obtained fresh and then frozen immediately at −80 degrees. Stool was then processed as previously described to obtain DNA samples (Wheeler et al.; Cell Host Microbe 2016). The resulting DNA was then sequenced at the 16S ribosomal RNA for bacteria and internal transcribed spacer (ITS) for fungi using the Illumina MySeq. The resulting sequence data was then analyzed with the Greengenes 16S database or the Underhill fungal database (published in Wheeler et al.). The resulting OTU (operational taxonomic unit) counts were then collated and analyzed on Microsoft Excel.

Mice will be implanted in their upper mammary fat pads with syngeneic PyMT mammary tumor cells as described above. Transplanted mice will be treated at 2 weeks or 30 days, when tumors are approximately 1.0 cm, tumor-bearing mice will then be divided into the appropriate experimental cohorts (10 mice/group) with treatment groups receiving RT with or without antibacterial and/or antifungal drug cocktails, versus the control group receiving water or antibiotics or antifungals alone with no RT. RT will consist of a single low dose (2 Gy), medium dose (16 Gy) or high dose (34 Gy). RT may also consist of a single dose at 12 Gy. The effect of multiple daily doses of low dose (2 Gy, 4 Gy) or high dose (6 Gy, 8 Gy) will also be tested (Table 1). RT will be administered to a local field centered on the transplanted mammary tumor using the XRAD SmART, delivering X-rays from 50-225 kV using different lead applicators to deliver beam sizes ranging from 0.5-2.0 cm or centered on the transplanted mammary tumor on the thorax avoiding the abdomen as much as possible to prevent irradiating the gut using 662 keV energy with a 1.06 Gy/min dose rate and a custom shielding apparatus machined from a solid lead block to collimate the radiation into 2 cm beams to more closely model how radiation is delivered to patients.

TABLE 1

Experimental Radiation Doses and Fractionation Schedules

| Radiation Dose | Fraction Size | Number of Fractions |
| --- | --- | --- |
| Low Dose | 2 Gy | 1 |
| Medium Dose | 16 Gy | 1 |
| High Dose | 34 Gy | 1 |
| Low Dose Fractionated | 2 Gy | 5 |
| Medium Dose Fractionated | 4 Gy | 5 |
| High Dose Fractionated | 8 Gy | 5 |

Figure 2:
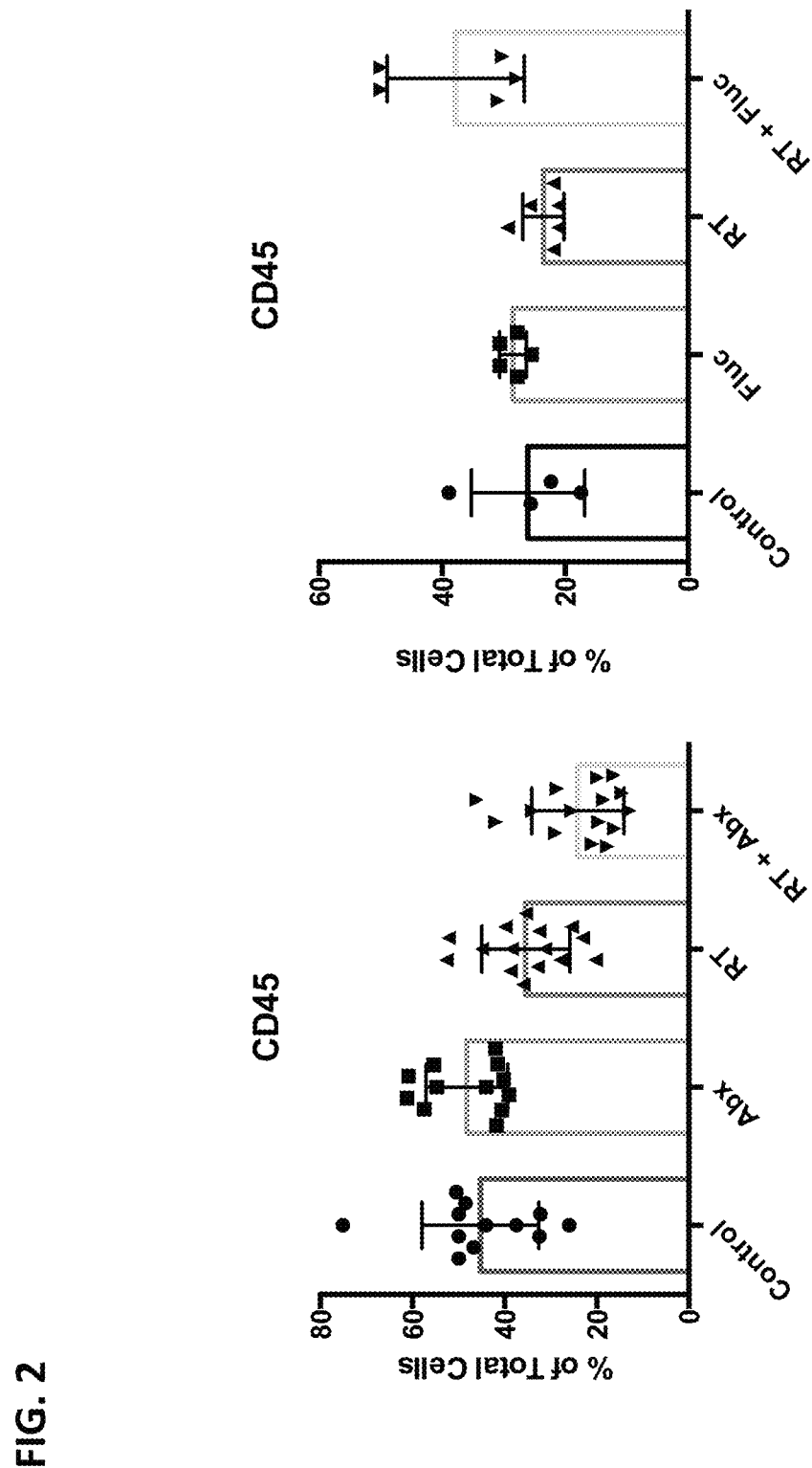
FIG. 2 depicts antibiotic treatment with RT reduces the number of intratumoral leukocytes, in accordance with various embodiments of the invention.
Figure 3:
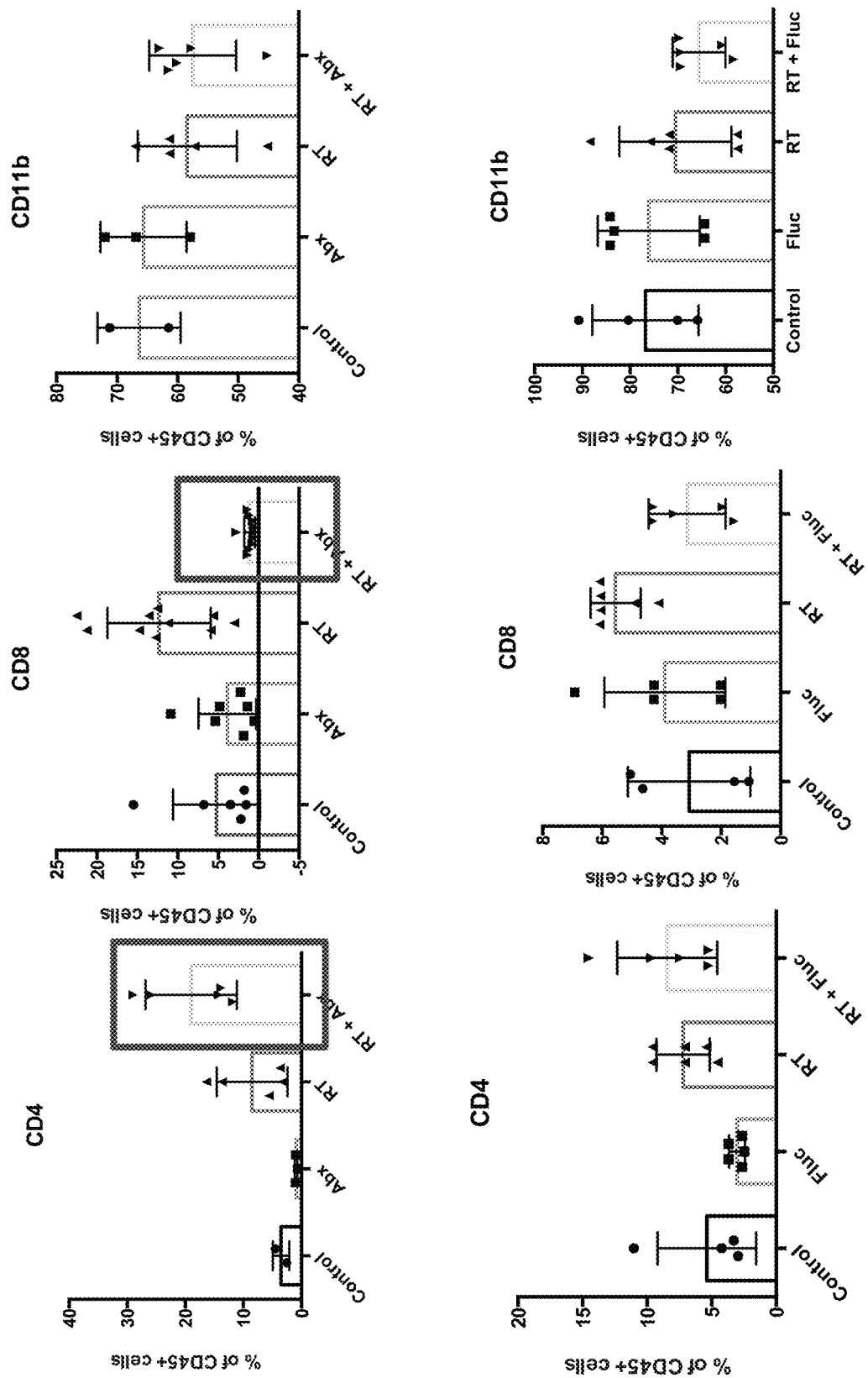
FIG. 3 depicts a marked increase in the CD4+ T cells and a reduction in CD8+ T cells with RT and antibiotics. The addition of fluconazole reduces the increase in CD4+ T cell and prevents the reduction of CD8+ T cells. Abx: Vancomycin, Colistin and Ampicillin.
Figure 4:
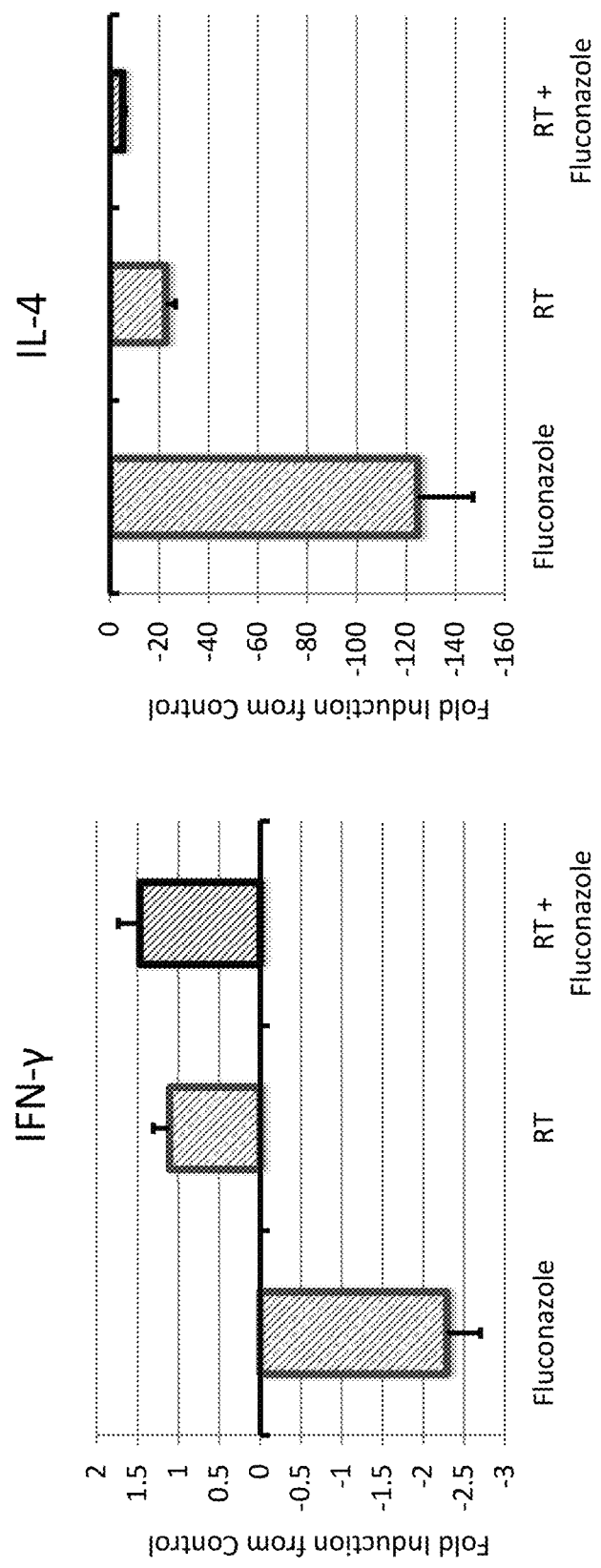
FIG. 4 depicts CD4+ T cells in fluconazole treated mice express more IFN-γ and less IL-4, in accordance with various embodiments of the invention.
Figure 13:
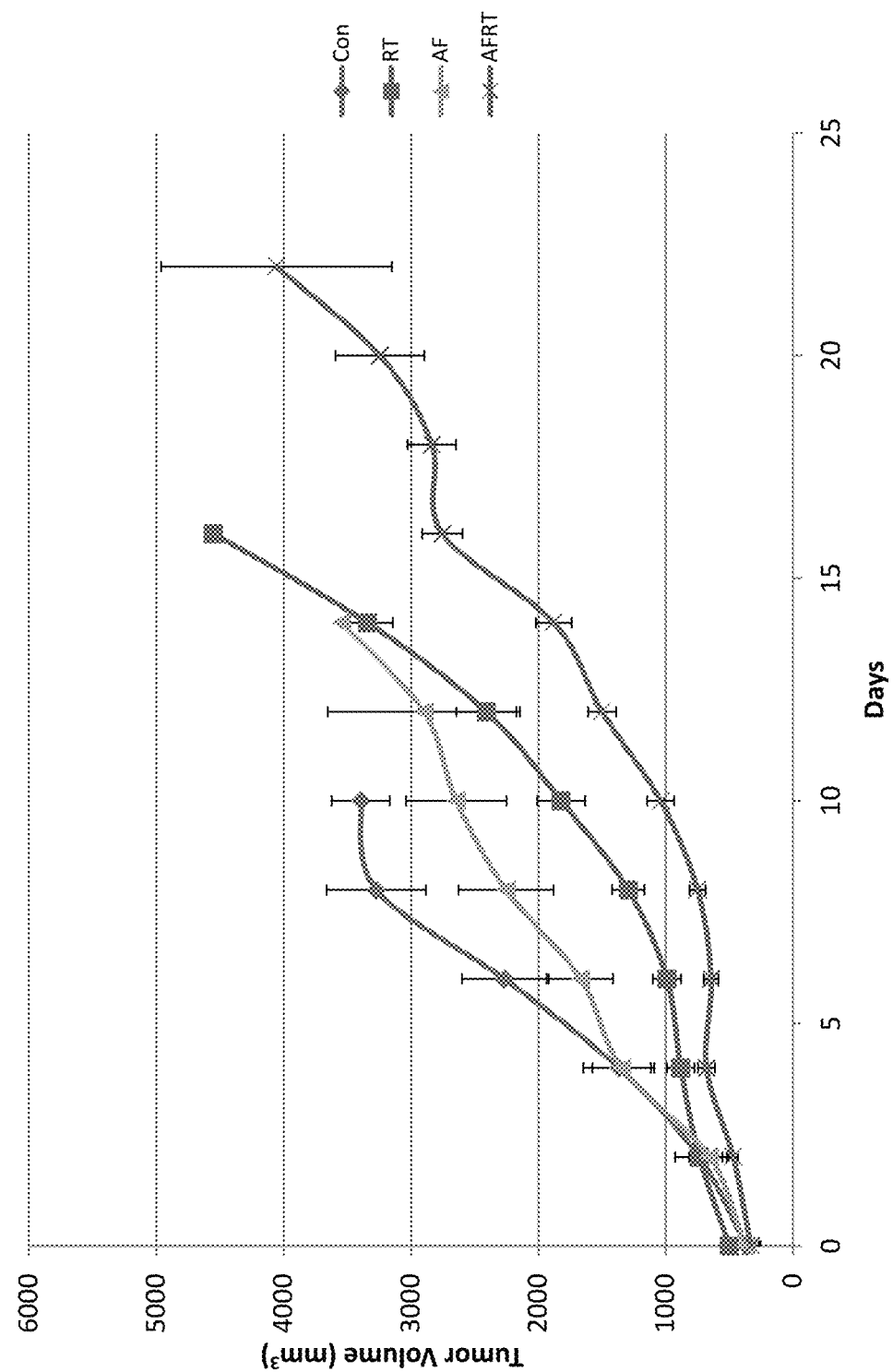
FIG. 13 depicts that combined antifungal treatment shows similar enhanced RT efficacy, in accordance with various embodiments of the invention. Antifungal: Fluconazole, 5FC, and/or Amphotericin B.

For experiments assessing antifungal treatment and the efficacy of radiation therapy (FIGS. 2 and 13), mice bearing syngeneic murine tumors (derived from the E0771 cell line) were treated for one week with fluconazole by putting fluconazole in their drinking water. When tumors reached approximately 1 cm in size they were irradiated with 16

Gray of focal radiation from a Cesium-137 source. The tumors were then followed for tumor growth until they reached approximately 2 cm in size at which time they were harvested for analysis.

Figure 14:
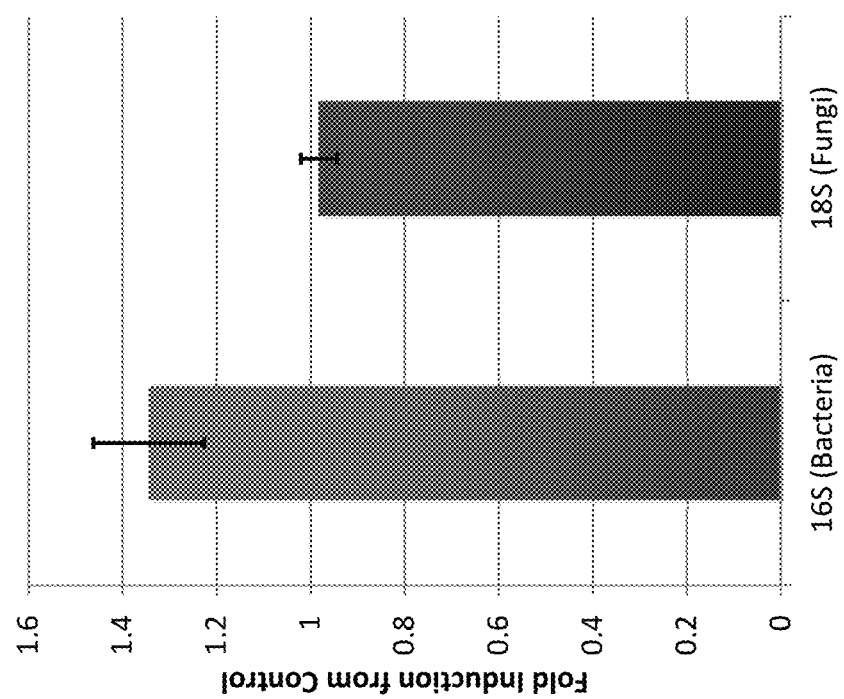
FIG. 14 depicts the effect of antifungal treatment on bacterial and fungal numbers.
Figure 15:
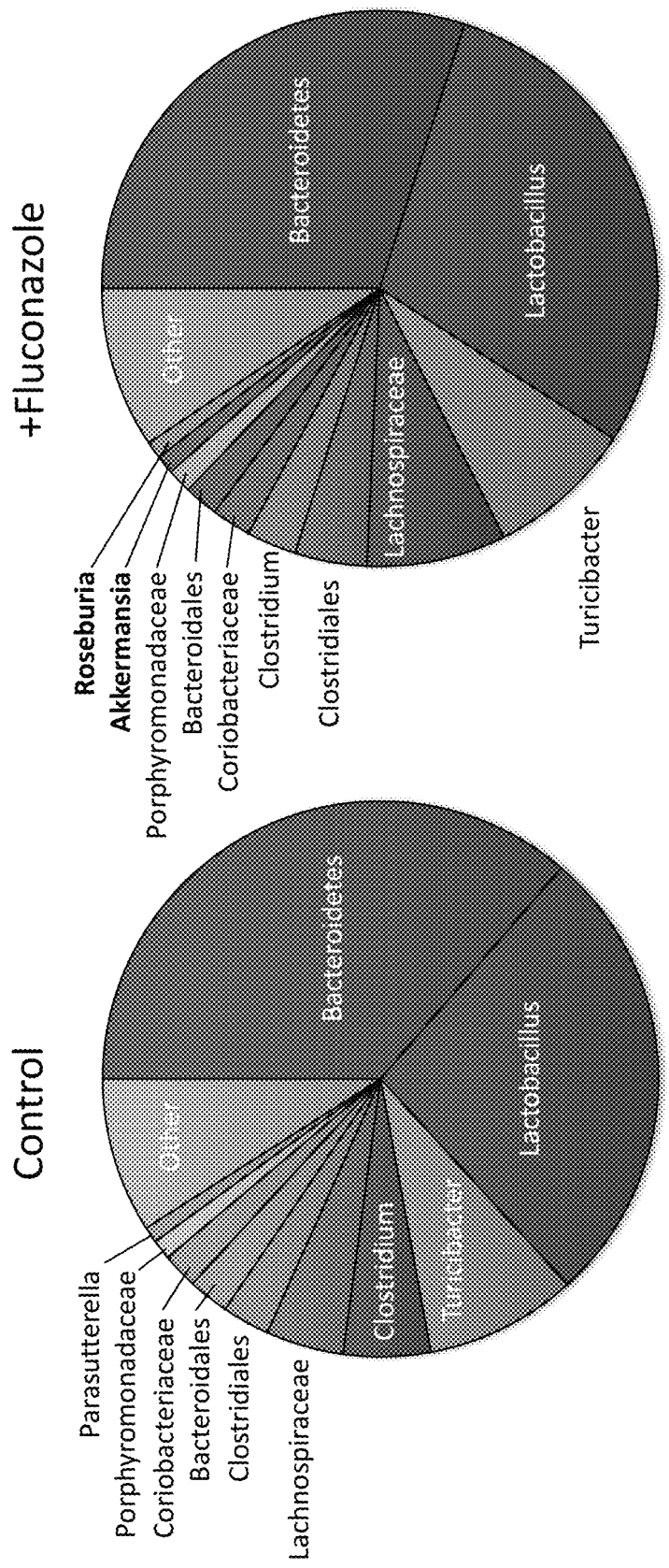
FIG. 15 depicts that antifungal treatment increases a few species of bacteria (*Akkermansia* and *Roseburia*), in accordance with various embodiments of the invention.
Figure 16:
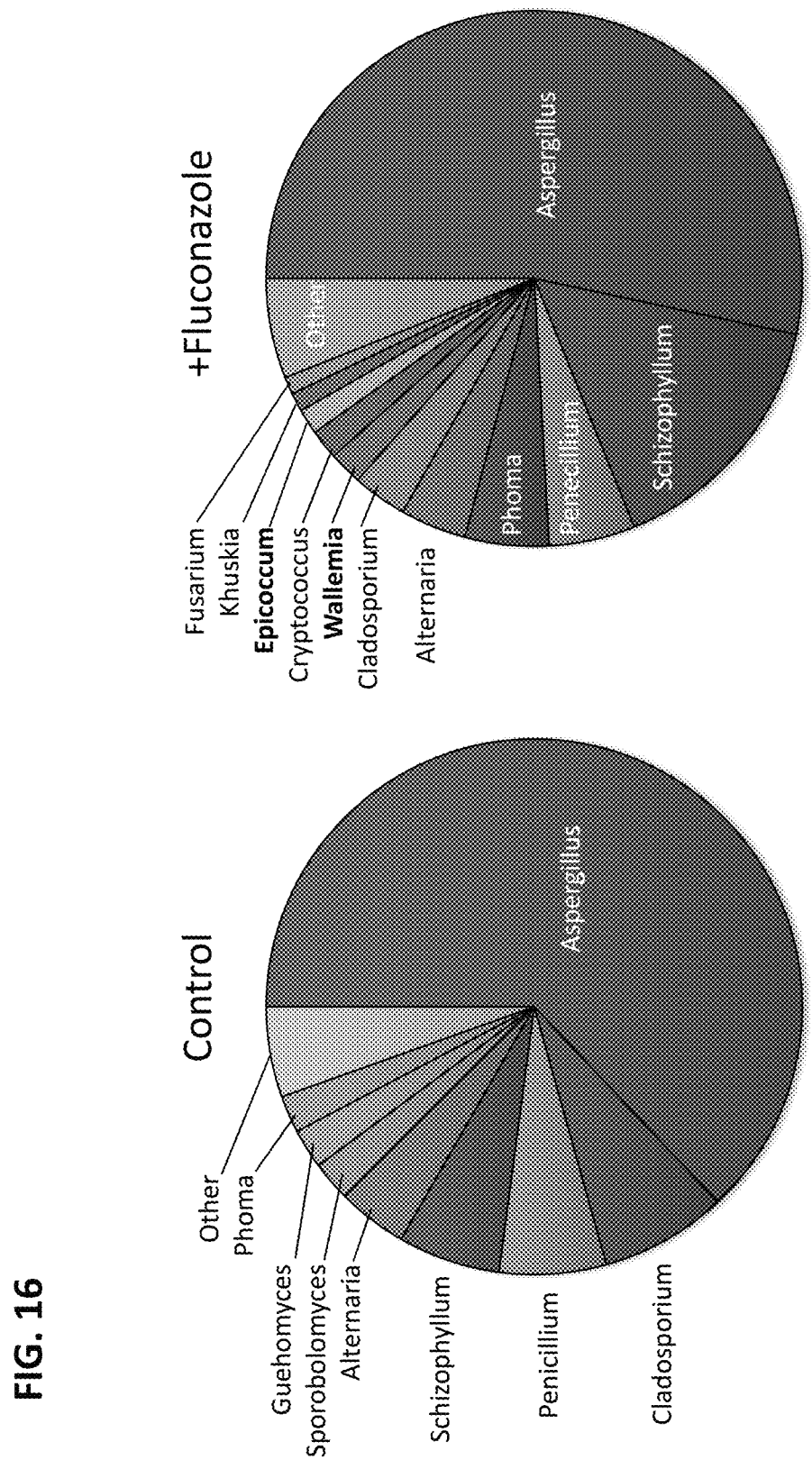
FIG. 16 depicts that antifungals also allow for increased representation of new species (*Wallemia* and *Epicoccum*), in accordance with various embodiments of the invention.
Figure 17:
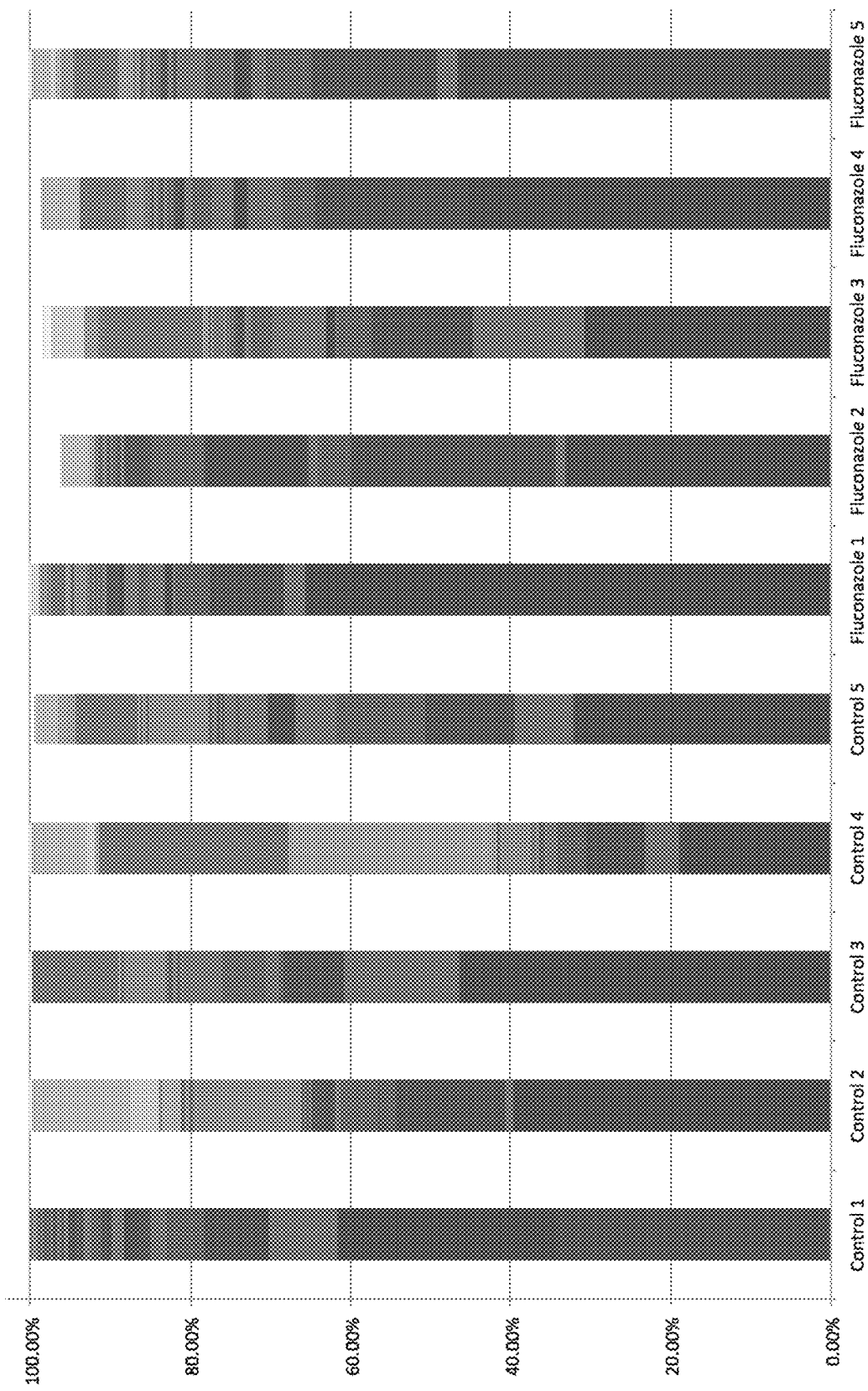
FIG. 17 depicts that a wide variation of species is observed both inter- and intra-treatment groups.
Figure 19:
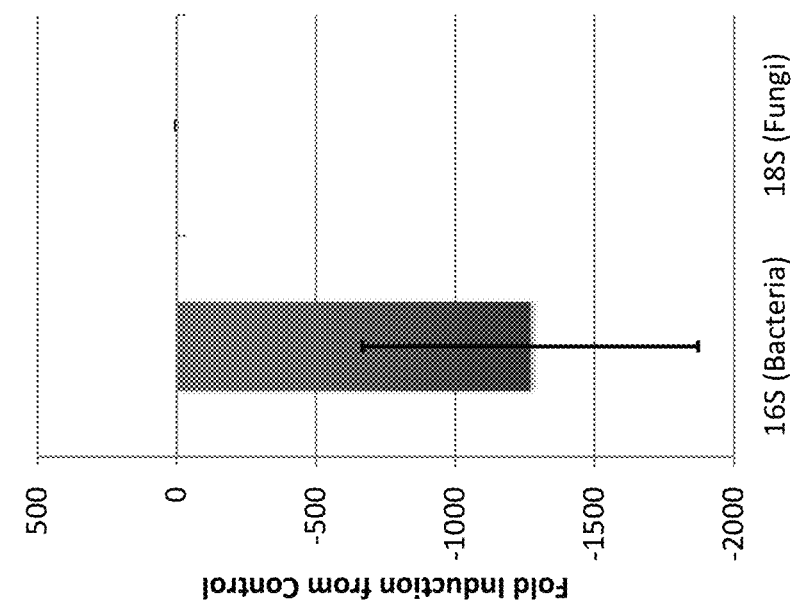
FIG. 19 depicts the effect of combined antibiotic and antifungal treatment on bacterial and fungal load. Abx: Vancomycin, Imipenem/cilastatin, Neomycin, and Fluconazole.
Figure 18:
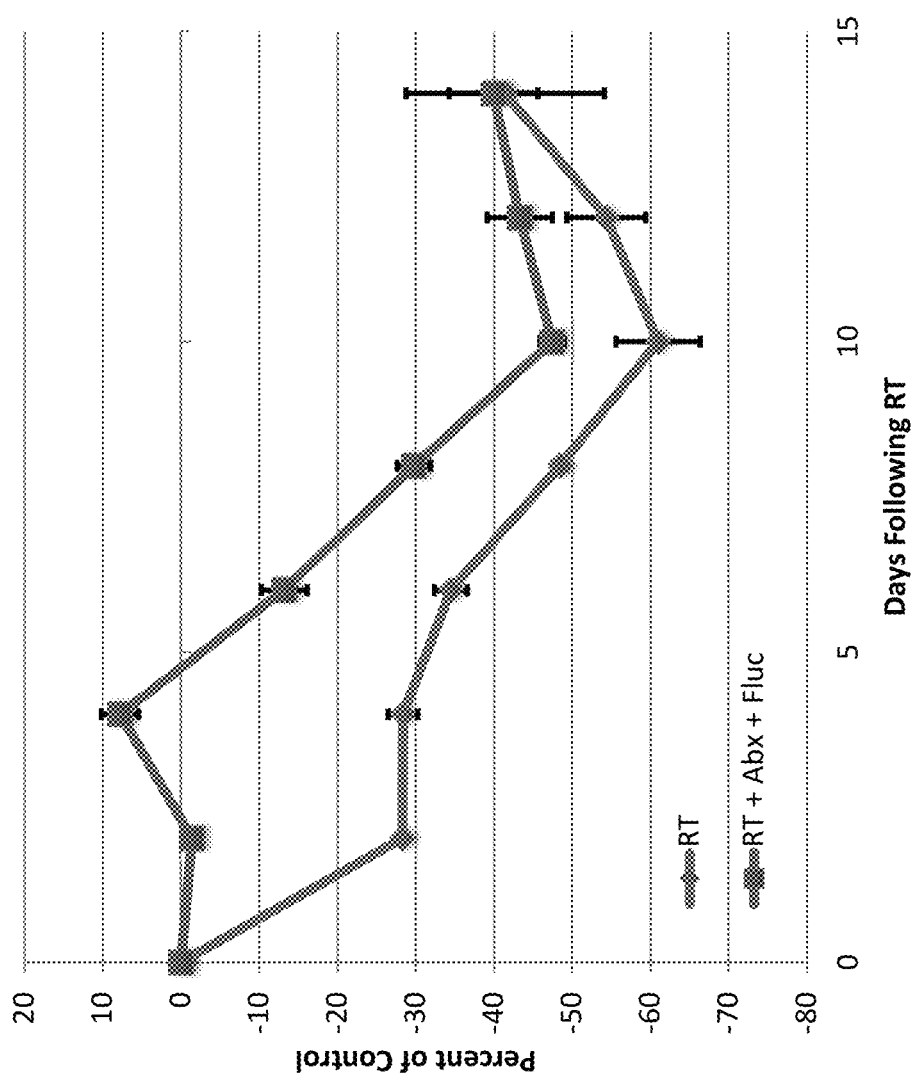
FIG. 18 depicts that combined antibiotic and antifungal treatment reduces the efficacy of RT. Abx: Vancomycin, Imipenem/cilastatin, Neomycin, and Fluconazole.
Figure 20:
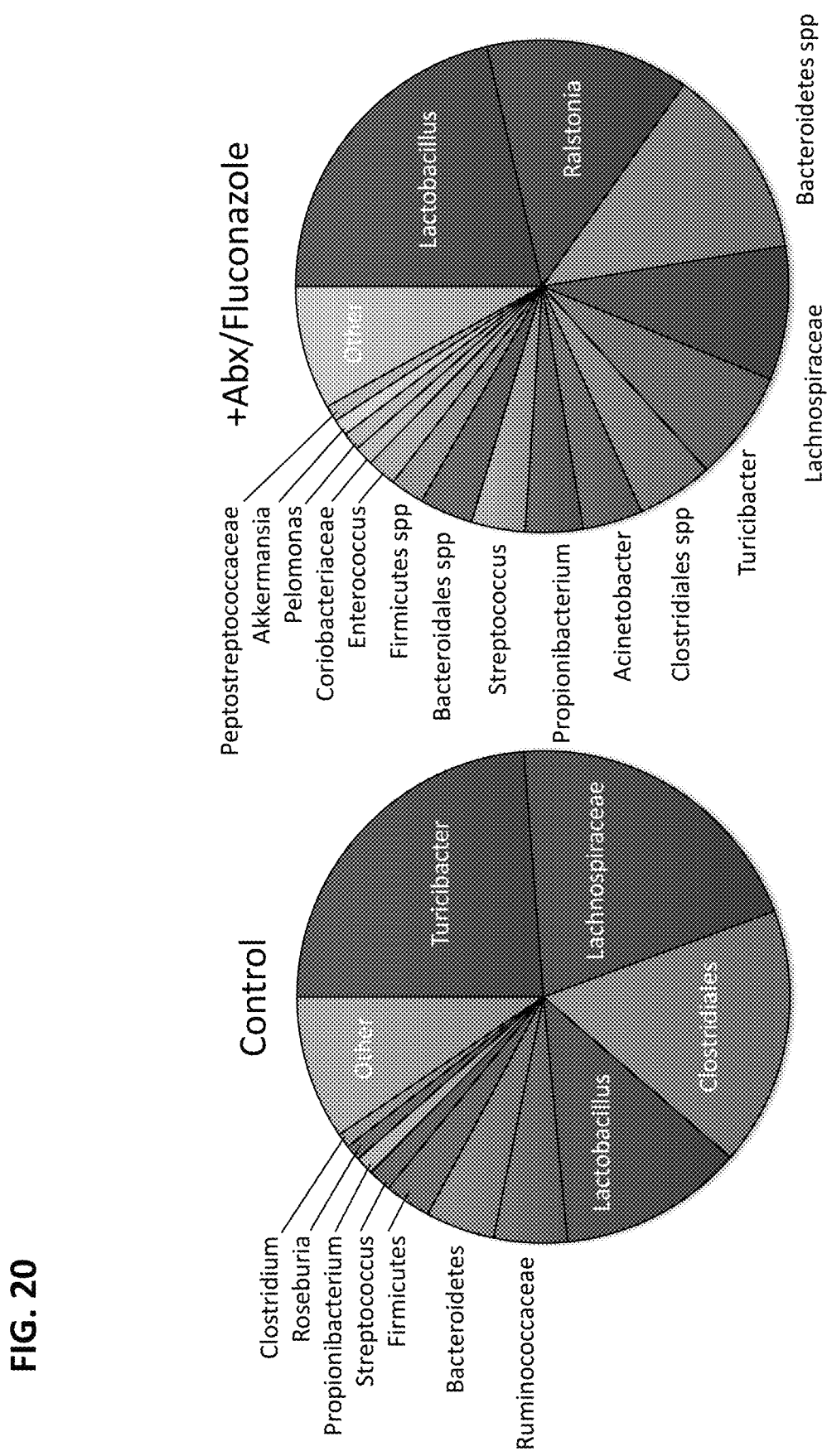
FIG. 20 depicts that combined treatment leads to even more representation of rare bacterial species, in accordance with various embodiments of the invention.
Figure 21:
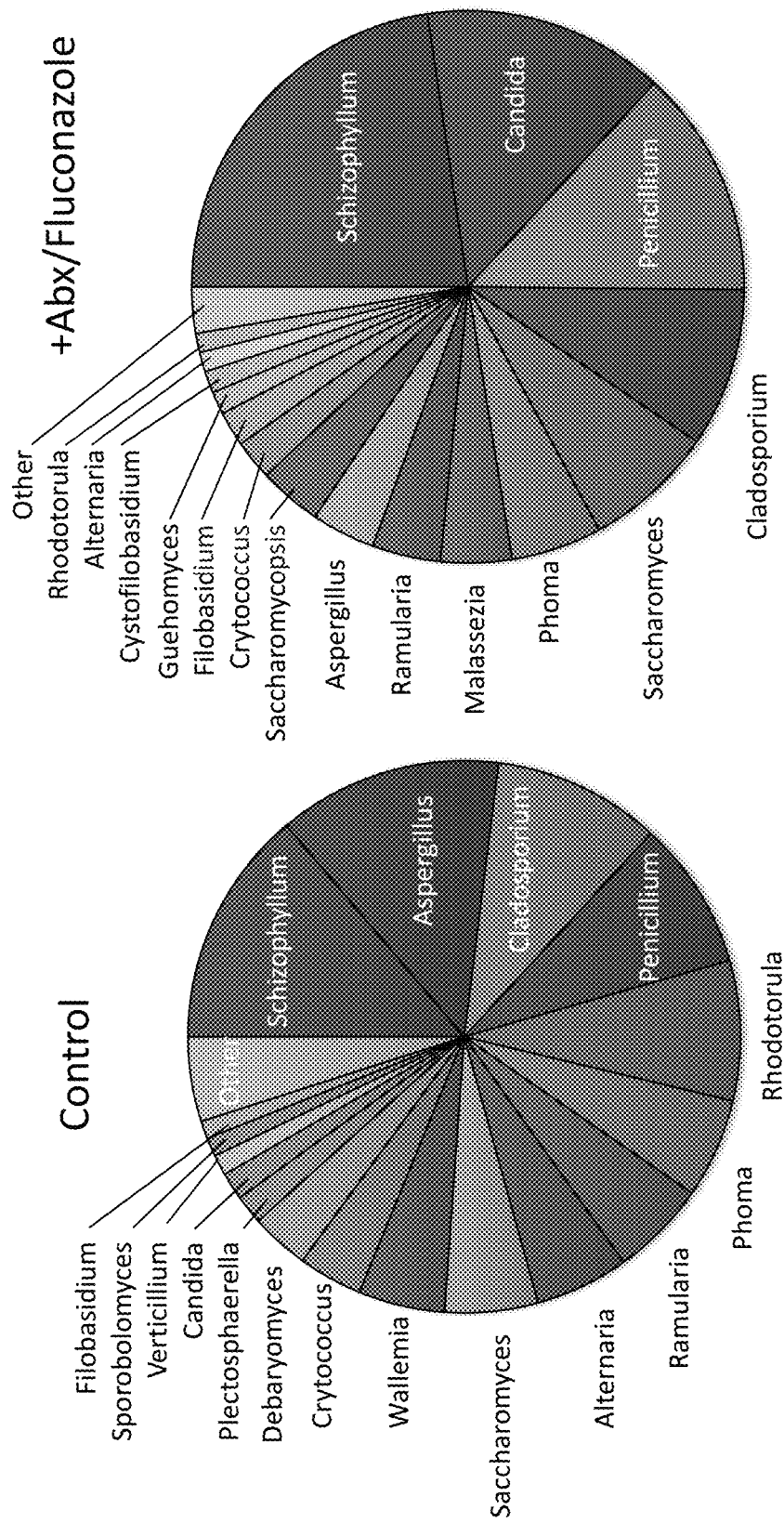
FIG. 21 depicts that combined treatment leads to even more representation of rare fungal species and eliminates some species seen with either treatment alone, in accordance with various embodiments of the invention.

For experiments assessing the anti-fungal combination treatment (FIG. 14), in addition to just fluconazole the mice were treated with a cocktail of antifungals (Fluconazole, 5-Fluorocytosine and Amphotericin B) for one week prior to RT.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating cancer or reducing tumor size in a subject in need thereof, comprising:
   administering to the subject, between one month and one day prior to initial commencement of cancer therapy treatment, a therapeutically effective amount of a composition comprising an anti-fungal agent that modulates a fungal population in the subject's gut; and
   administering to the subject a therapeutically effective amount of a cancer therapy,
   wherein the administration of the composition modulates a fungal population in the subject's gut and enhances the therapeutic response or anti-tumor response to the cancer therapy, and
   wherein the cancer therapy is selected from the group consisting of radiation therapy (RT), chemotherapy, immunotherapy, targeted therapy and combinations thereof.

2. The method of claim 1, wherein the cancer is breast cancer.

3. The method of claim 1, wherein the anti-fungal agent causes a decrease in the fungal population.

4. The method of claim 3, wherein the fungal populations decreased are *Aspergillus, Cladosporium, Phoma, Guehomyces, Candida tropicalis* or combinations thereof.

5. The method of claim 1, wherein the anti-fungal agent is fluconazole, 5-flurocytosine, amphotericin B or a combination thereof.

6. The method of claim 1, wherein the cancer therapy is RT and the RT is administered in a dosage between 2Gy to 34Gy.

7. The method of claim 6, wherein the RT is administered for 1 to 7 weeks.

8. A method of enhancing the efficacy of a cancer therapy in a subject in need thereof, comprising:
   administering to the subject, between one month and one day prior to initial commencement of the cancer therapy treatment, a therapeutically effective amount of an anti-fungal agent that modulates a fungal population in the subject's gut; and
   administering to the subject a therapeutically effective amount of the cancer therapy wherein the cancer therapy is selected from the group consisting of radiation therapy (RT), chemotherapy, immunotherapy, targeted therapy and combinations thereof, and thereby enhance the efficacy of the cancer therapy in the subject.

9. The method of claim 8, wherein the subject is a subject with breast cancer.

10. The method of claim 8, wherein administering the anti-fungal agent and cancer therapy prolongs the delay in tumor regrowth compared to non-treated tumors.

11. The method of claim 8, wherein the anti-fungal agent causes a decrease in a fungal population.

12. The method of claim 8, wherein the anti-fungal agent is fluconazole, 5-flurocytosine and amphotericin B.

13. The method of claim 8, wherein the cancer therapy is radiation therapy (RT).

14. The method of claim 1, comprising administering, 3 weeks prior to cancer therapy treatment, the composition comprising the anti-fungal agent.

15. The method of claim 1, comprising administering, 2 weeks prior to cancer therapy treatment, the composition comprising the anti-fungal agent.

16. The method of claim 1, comprising administering, 1 week prior to cancer therapy treatment, the composition comprising the anti-fungal agent.

17. The method of claim 8, comprising administering, 3 weeks prior to cancer therapy treatment, the composition comprising the anti-fungal agent.

18. The method of claim 8, comprising administering, 2 weeks prior to cancer therapy treatment, the composition comprising the anti-fungal agent.

19. The method of claim 8, comprising administering, 1 week prior to cancer therapy treatment, the composition comprising the anti-fungal agent.

20. The method of claim 1, further comprising continuing to administer the composition comprising the anti-fungal agent concurrently or simultaneously with the cancer therapy.

21. The method of claim 8, further comprising continuing to administer the anti-fungal agent concurrently or simultaneously with the cancer therapy.

* * * * *